United States Patent
Nishii et al.

[11] Patent Number: 5,403,815
[45] Date of Patent: Apr. 4, 1995

[54] TRIAZINE DERIVATIVE AND A HERBICIDE COMPRISING THE SAME AS AN EFFECTIVE INGREDIENT

[75] Inventors: Masahiro Nishii, Sodegauramachi; Izumi Kobayashi, Tokyo; Masatoshi Uemura, Sodegauramachi; Tetsuo Takematsu, Utsunomiya, all of Japan

[73] Assignee: Idemitsu Kosan Company Limited, Tokyo, Japan

[21] Appl. No.: 180,654

[22] Filed: Jan. 12, 1994

Related U.S. Application Data

[62] Division of Ser. No. 582,835, Oct. 5, 1990, Pat. No. 5,290,754.

[30] Foreign Application Priority Data

Feb. 20, 1989 [JP] Japan ................................. 1-38178
Jun. 19, 1989 [JP] Japan ................................. 1-154465

[51] Int. Cl.⁶ ..................... A01N 43/68; C07D 251/18
[52] U.S. Cl. .......................... 504/230; 544/207
[58] Field of Search ..................... 504/230; 544/207

[56] References Cited

U.S. PATENT DOCUMENTS

| | | | |
|---|---|---|---|
| 4,844,731 | 7/1989 | Takematsu et al. | 71/93 |
| 4,932,998 | 6/1990 | Takematsu et al. | 71/90 |
| 5,169,425 | 8/1992 | Takematsu et al. | 71/88 |
| 5,234,893 | 8/1993 | Hirata et al. | 504/133 |

FOREIGN PATENT DOCUMENTS

| | | |
|---|---|---|
| 63-51379 | 3/1988 | Japan. |
| 63-14676 | 6/1988 | Japan. |
| 63-238071 | 10/1988 | Japan. |
| 63-264465 | 11/1988 | Japan. |
| WO88/02368 | 4/1988 | WIPO. |

OTHER PUBLICATIONS

Chemical Abstracts, vol. 112, 1990, Takematsu et al., p. 772, abstract No. 178993v, Columbus, Ohio, US; of JP-A-01 246 279 (Oct. 1989).

*Primary Examiner*—John M. Ford
*Attorney, Agent, or Firm*—Frishauf, Holtz, Goodman & Woodward

[57] ABSTRACT

A triazine compound of the formula

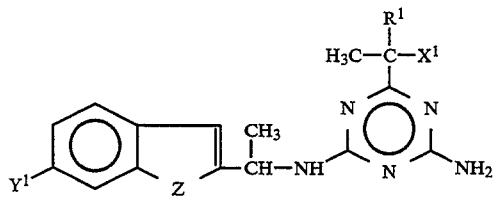

wherein $Y^1$ is a hydrogen atom or a methyl group and Z is an oxygen atom or a sulfur atom, $X^1$ is a halogen atom and R is a hydrogen atom, a methyl group or an ethyl group. The triazine compound is useful as a herbicide for combatting weeds.

22 Claims, No Drawings

TRIAZINE DERIVATIVE AND A HERBICIDE COMPRISING THE SAME AS AN EFFECTIVE INGREDIENT

This is a division of application Ser. No. 07/582,835 filed Oct. 5, 1990, which is the United States designated application of PCT/JP90/00194 filed Feb. 19, 1990, now U.S. Pat. No. 5,290,754 issued Mar. 1, 1994.

FIELD OF TECHNOLOGY

The present invention relates to novel triazine derivatives and a herbicide containing the derivatives as an effective ingredient.

BACKGROUND TECHNOLOGY

A variety of herbicides have been hitherto developed and contributed to the productivity and labor-saving in agriculture. However, certain kinds of herbicides have been used over so long years that population of troublesome weeds withstanding them are increasing so that appearance is desired of a herbicids having a broad herbicidal spectrum and effectiveness also against these troublesome weeds. It is also desired to develop a high-activity herbicide in order to overcome the problem of environmental pollution by conventional herbicides. In order to overcome to the problem of the ununiform germination of weeds over a long period of time, furthermore, appearance is also awaited of a herbicide exhibiting excellent persistent effectiveness and having a versatility of treatment to exhibit effectiveness even by treatment over a wide range of period from the pre-germination stage to the growing period of weeds.

The inventors have continued investigations to develop a herbicide capable of exhibiting an excellent herbicidal effect against various kinds of annual and perennial weeds without causing phytotoxicity to paddy rice and arrived at a discovery that a herbicide containing a triazine compound as an effective ingredient is effective (official publication of Japanese Patent Toku-sai-hyo 88/02368, official publication of Japanese Patent Kokai 63-146876, official publication of Japanese Patent Kokai 63-51379 and official publication of Japanese Patent Kokai 63-264465). This triazine-based herbicide is highly active against troublesome weeds in paddy rice field at low dosage without phytotoxicity to-paddy rice plant. This herbicide also shows excellent herbicidal activity against troublesome weeds by foliage application in upland field without phytotoxicity to Gramineous crops.

Nevertheless, this herbicide shows somewhat limited performance by preemergence treatment to the soil in upland fields.

DISCLOSURE OF THE INVENTION

The present invention provides:
(1) a triazine derivative represented by the general formula

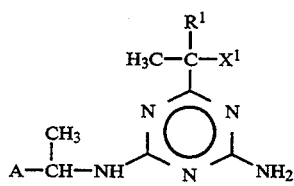

[in the formula, A denotes

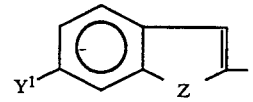

(in which $Y^1$ denotes a hydrogen atom or a methyl group and Z denotes an oxygen atom or a sulfur atom),

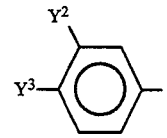

(in which $Y^2$ and $Y^3$, which can be of the same kind or different kinds each denote a methyl group or a methoxy group) or

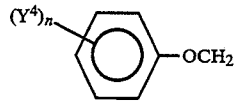

(in which $Y^4$ denotes a methyl group, trifluoromethyl group, methoxy group or fluorine atom and n denotes an integer of 0 to 2), $X^1$ denotes a halogen atom and $R^1$ denotes hydrogen, a methyl group or an ethyl group],
and (2) a herbicide containing, as an effective ingredient, a triazine derivative represented by the general formula

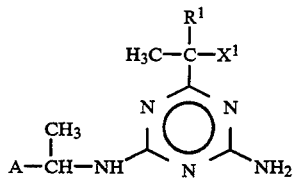

[in the formula, A denotes

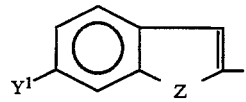

(in which $Y^1$ denotes a hydrogen atom or a methyl group and Z denotes an oxygen atom or a sulfur atom),

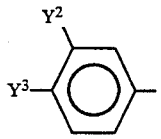

(in which $Y^2$ and $Y^3$, which can be of the same kind or different kinds, each denote a methyl group or a methoxy group) or

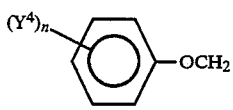

(in which Y⁴ denotes a methyl group, trifluoromethyl group, methoxy group or fluorine atom and n denotes an integer of 0 to 2), X¹ denotes a halogen atom and R¹ denotes hydrogen, a methyl group or an ethyl group].

The inventors have continued investigations to search a compound free from phytotoxicity to the crops of the family of Gramineae in upland fields capable of exhibiting a high herbicidal effect against troublesome weeds both in the treatment to soil and in the treatment to foliage with an excellent effect of soil treatment in paddy fields. As a result, a discovery has been reached that those having a specific haloalkyl group are effective leading to completion of the present invention.

The triazine derivative of the present invention is a novel compound and can be effectively utilized as a herbicide. When used as a herbicide for upland fields, the herbicide of the present invention containing the triazine derivative as an effective ingredient can be used over a long term for appropriate chemical treatment as compared with existing herbicides for upland fields and exhibits a high activity against troublesome weeds both in the soil treatment before germination and in the course of germination of the weeds and in the foliage treatment during the growth period of the weeds still without phytotoxicity to crops. In particular, a remarkably high effect is obtained by the soil treatment or treatment to foliage in non-paddy fields of crops belonging to Gramineous crops. As compared with existing herbicides for paddy rice, in addition, the herbicide of the present invention has a high chemical effect against hardly eliminable weeds still with little phytotoxicity.

BEST MODE TO PRACTICE THE INVENTION

The present invention provides a triazine derivative represented by the general formula

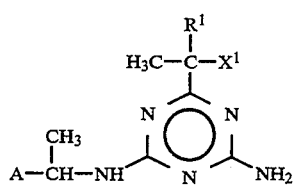

[in the formula, A denotes

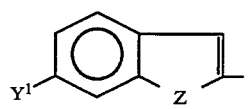

(in which Y¹ denotes a hydrogen atoms or a methyl group and Z denotes an oxygen atom or a sulfur atom),

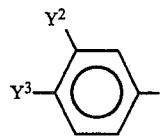

(in which Y² and Y³, which can be of the same kind or of different kinds, each denote a methyl group or a methoxy group) or

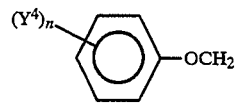

(in which Y⁴ denotes a methyl group, trifluoromethyl group, methoxy group or fluorine atom and n denotes an integer of 0 to 2), X¹ denotes a halogen atom and R¹ denotes hydrogen, a methyl group or an ethyl group] and also provides a herbicide containing the triazine derivative represented by the above given general formula [I].

The triazine derivative of the present invention represented by the above given general formula [I] can be prepared by various different methods. The method of preparation with the highest efficiency among them is the method to react an alkyl amine salt represented by the general formula

[in the formula, A is the same as given above and X³ denotes a halogen atom] and cyanoguanidine expressed by the formula

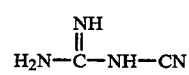

to prepare an alkyl biguanide salt represented by the general formula

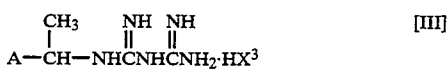

[in the formula, A and X³ are each the same as given above] and then to react the alkyl biguanide salt with an alkyl ester represented by the general formula

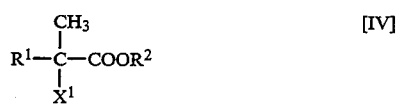

[in the formula, R¹ and X¹ are each the same as given above and R² denotes an alkyl group having 1 to 4 carbon atoms]. In this manner, the alkyl amine salt represented by the general formula [II] and cyanoguanidine are reacted to give the alkyl biguanide salt represented by the general formula [III] which is reacted with the alkyl ester represented by the general formula [IV] to give the desired triazine derivative represented by the general formula [I] in high efficiency.

In conducting the reaction between the alkyl amine salt represented by the above given general formula [II] and cyanoguanidine here, these two compounds can be used in an approximately equimolar proportion and usable solvents include cyclic hydrocarbons such as benzene, Decalin, alkyl naphthalenes and the like and chlorinated hydrocarbons such as carbon tetrachloride, ethylene dichloride, chlorobenzene, dichlorobenzene, trichlorobenzene and the like. And, the reaction temperature is not particularly limitative and sufficient proceeding can be obtained in the range from low to high temperatures or, in particular, from 80° to 200° C.

The salt of an alkyl biguanide derivative represented by the general formula [III] is obtained by this reaction and, in the method of the present invention, this is reacted with the alkyl ester of the general formula [IV]

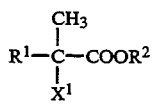

prepare the desired triazine derivative represented by the general formula [I]. This reaction usually proceeds in high efficiency at about 10° to 100° C. in the presence of a catalyst such as a base and the like in a solvent such as alcohols, e.g., methanol, ethanol, isopropanol and the like, various kinds of ketones, aliphatic hydrocarbons, various kinds of ethers, various kinds of cyclic hydrocarbons, chlorinated hydrocarbons and the like.

The triazine derivatives of the general formula [I] obtained by the above described method are each a novel compounds.

And, the compound of the present invention has optical isomers and is obtained usually as a racemic modification while it is possible to obtain the respective antipodes by a known method such as asymmetric synthesis. The compound of the present invention can be used as a herbicide either in the form of the racemic modification or in the form of the isolated optical isomer. Furthermore, the compound of the present invention also can be used as a herbicide in the form of a salt of an inorganic acid or organic acid.

Furthermore, the triazine derivative represented by the general formula [I] inhibits germination and growth of weeds and has high selectivity so that it is satisfactory as a herbicide. In addition, it is useful not only for the soil treatment before the germination of weeds as a matter of course but also for the foliage treatment to the growing weeds to have a versatility of the chemical treatment. The triazine derivative of the present invention exhibits no phytotoxicity to the crops belonging to Gramineous crops such as corn, grain sorghum, wheat, barley, oat and the like as the important crops in upland fields and exhibits a prominent herbicidal effect against strongly troublesome broadleaf weeds such as *Cassia obtusifolia L., Ipomoea purpurea, Abutilon theophrasti, Galium sparium var. echincsoermcn, Stellaria media, Veronica persica, Polygonum persicaria, Viola arvensis, Brassica juncea, Amaranthus patulus,* Common blackjack and the like and strongly harmful weeds belonging to the family of Graminea such as *Digitaria sanguinalis, Alopecurus myosuroides* and the like.

Furthermore, this triazine derivative not only exhibits a prominent herbicidal effect against broadleaf weeds such as *Rotala indica* (Willd) *Koehne var. uligirosa* (Miq.) *Koehne, Lindernia pyxidaria L., Monochoria vaginalis Presl var. plantaginea* and the like, weeds belonging to the family of Cyperaceae such as *Cyperus difformis L.* and the like and weeds belonging to the family of Gramineae such as *Echinochloa crus-galli P. Beauv. vat. formosensis Ohwi* and the like but also exhibits a prominent herbicidal effect against perennial weeds such as *Scirpus juncoides Roxb. ssp. Hotarui Ohwi T. Koyama, Cyperus serotinus Rottb., Sagittaria pygmaea Miq.* and the like, which are currently deemed to be hardly eliminable, without causing chemical damages against paddy rice.

In the next place, the herbicide of the present invention contains the above described compound or, namely, the triazine derivative represented by the general formula [I] as the effective ingredient and these compounds can be used as being prepared in the preparation form such as a water-dispersible powder, emulsion, dust, granules, flowable agent, solution and the like by mixing with a liquid carrier such as solvents and the like or a solid carrier such as mineral fine powders and the like. In the preparation of the form, it is optional according to need to add an emulsifying agent, dispersion aid, spreading agent, suspending agent, penetrating agent, stabilizer and other adjuvants.

When the herbicide of the present invention is used in the form of a water-dispersible powder, usually, a composition to be used is prepared by compounding from 10 to 55% by weight of the above described triazine derivative of the present invention as the effective ingredient, from 40 to 88% by weight of a solid carried and from 2 to 5% by weight of a surface active agent. Further, when it is used in the form of an emulsion or a flowable agent, it can be usually prepared by compounding from 5 to 50% by weight of the triazine derivative of the present invention as the effective ingredient, from 35 to 90% by weight of a solvent and a surface active agent and from 5 to 15% by weight of other adjuvants.

When it is used in the form of a dust, on the other hand, it can be prepared usually by compounding from 1 to 15% by weight of the triazine derivative of the present invention as the effective ingredient and from 85 to 99% by weight of a solid carrier. When it is used in the form of granules, furthermore, they can be prepared usually by compounding from 0.1 to 15% by weight of the triazine derivative of the present invention as the effective ingredient, from 80 to 97.9% by weight of a solid carrier and from 2 to 5% by weight of a surface active agent. The solid carrier used here is a fine mineral powder and such a fine mineral powder includes diatomaceous earth, oxides such as hydrated lime and the like, phosphates such as apatite and the like, sulfates such as gypsum and the like, silicates such as talc, pyrophyllite, clay, kaolin, bentonitc, acid clay, white carbon, quartz powder, silica stone powder and the like, and so on.

And, the liquid carrier includes organic solvents such as paraffinic or naphthenic hydrocarbons, e.g., kerosine, mineral oil, spindle oil and the like, aromatic hydrocarbons, e.g., benzene, toluene, xylene and the like, chlorinated hydrocarbons, e.g., 2-chlorotoluene, trichloromethane, trichloroethylene and the like, alcohols, e.g., cyclohexanol, amyl alcohol, ethylene glycol and the like, alcohol ethers, e.g., ethylene glycol monomethyl ether, ethylene glycol monoethyl ether and the like, ketones, e.g., isophorone, cyclohexanone, cyclohexenyl cyclohexanone and the like, ethers, e.g., Butyl Cellosolve, dimethyl ether, methyl ethyl ether and the like, esters, e.g., isopropyl acetate, benzyl acetate, methyl phthalate and the like, amides e.g., dimethyl formamide and the like, nitriles, e.g., acetonitrile, propionitrile and the like, and sulfoxides, e.g., dimethyl sulfoxide and the like as well as mixtures thereof, water and the like.

Further, as the surface active agent, any one can be used among the anionic type ones (alkylbenzene sulfonates, alkyl sulfonates, lauric acid amide sulfonate and the like), nonionic type ones (polyoxyethylene octyl ether, polyethylene glycol laurate, sorbitan alkyl esters and the like), cationic type ones (dimethyl lauryl benzyl ammonium chloride, lauryl amine, stearyl trimethyl ammonium chloride and the like) and amphoteric type ones (amino acids, betaine and the like).

Further, it is optional with an object to improve the nature of the preparation form and to enhance the herbicidal effect that the compound of the present invention is used in combination with a polymeric compound or adjuvant such as sodium alginate, carboxymethyl cellulose, carboxy vinyl polymer, gum arabic, hydroxypropyl methyl cellulose and the like.

The above described triazine derivative of the present invention as a novel compound represented by the general formula [I] exhibits an excellent effect as a high-selectivity herbicide not causing any phytotoxicity for the crops in non-paddy fields such as corn, grain sorghum, wheat, barley, oat and the like by the soil treatment or foliage treatment either before germination or after germination of weeds. And, the herbicidal effect is high not only against annual weeds as a matter of course but also against perennial weeds and it is very useful as a high-selecte herbicide not causing any phytotoxicity also for paddy rice.

The herbicide of the present invention is administered in a dose of approximately from 0.1 to 1000 g or, preferably, from 1 to 100 g per 10 ares as the effective ingredient. When it is applied on foliage of plants, it is administered as being diluted to about 1 to 10000 ppm or, preferably, to 10 to 1000 ppm.

Incidentally, it is optional to use the triazine derivative represented by the general formula [I] in combination with other herbicidal constituents as the effective ingredient of the herbicide of the present invention. Such an auxiliary herbicidal constituent can be a herbicide hitherto on the market including various ones exemplified, for example, by the phenoxy-type herbicides, diphenyl ether-type herbicides, triazine-type herbicides, urea-type herbicides, carbamate-type herbicides, thiol carbamate-type herbicides, acid anilide-type herbicides, pyrazole-type herbicides, phosphoric acid-type herbicides, sulfonyl urea-type herbicides, nitrile-type herbicides, dinitroaniline-type herbicides, imidazolinone-type herbicides, oxadiazone and the like.

Furthermore, the herbicide of the present invention can be used as mixture with insecticides, germicides, growth-controlling agents of plants, fertilizers and the like according to need.

EXAMPLES

In the following, the present invention is described in further detail by way of examples.

PREPARATION EXAMPLE 1

Sodium methoxide was produced by gradually adding 0.92 g (40 m moles) of sodium to 20 ml of dried methanol and 2-(3',5'-dimethylphenoxy) isopropyl biguanide hydrochloride (20 m moles) (described in the official publication of Japanese Patent Kokai No. 63-264465) as the starting material I was added thereto and agitated for 30 minutes at room temperature. In the next place, 4.80 ml (40 m moles) of ethyl ester of $\alpha$-fluoro-$\alpha$-methyl propionic acid as the starting material II were added dropwise and agitated for 10 hours at room temperature. After completion of the reaction, the content material was poured into 100 ml of water and subjected to three times of extraction with 50 ml of ethyl acetate. This ethyl acetate layer was dried with anhydrous sodium sulfate followed by removal of the ethyl acetate by distillation under reduced pressure. The residue was purified by the silica gel column chromatography (developing solvent: hexane/ethyl acetate=4/1) followed by recrystallization from hexane-ethyl ether to give white 2-amino-4-[2-( 3', 5'-dimethylphenoxy) isopropylamino]-6-fluoroisopropyl-s-triazine (compound I). The produced amount, % yield, results of analysis, structural formula and others thereof are shown in Tables 1 to 3.

PREPARATION EXAMPLES 2 to 41

Compounds 2 to 41 were obtained by conducting the same procedure as in Preparation Example 1 excepting the use of 20 m moles of the alkyl biguanide hydrochloride (described in the official publication of Japanese Patent Toku-Sai-Hyo No. 88/02368, official publication of Japanese Patent Kokai No. 63-51379 and official publication of Japanese Patent Kokai No. 63-264465) indicated in Table 1 in place of the 2-(3',5'-dimethylphenoxy) isopropyl biguanide hydrochloride as the starting material I in Preparation Example 1 and the use of 20 m moles of the ester indicated in Table 1 in place of the ethyl ester of $\alpha$-fluoro-$\alpha$-methyl propionic acid as the starting material II. The produced amounts, % yields, results of analysis, structural formulas and others of these compounds are shown in Tables 1 to 3.

TABLE 1

| Preparation Example No. (Compound No.) | Starting Materials | | Yield (g) | Yield (%) | Melting Point (°C.) | Elementary Analysis (%) | | |
|---|---|---|---|---|---|---|---|---|
| | I | II | | | | C | H | N |
| Preparation Example 1 (Compound No. 1) | 2-(3',5'-dimethyl-phenoxy)-1-methyl-ethyl biganide | $\alpha$-fluoro, $\alpha$-methyl propionic acid ethyl ester | 2.53 | 38 | 102.4– 104.9 | 53.9 (61.2) | 7.3 (7.3) | 21.0 (21.0) |
| Preparation Example 2 (Compound No. 2) | 2-(3',5'-dimethyl-phenoxy)-1-methyl-ethyl biganide | $\alpha$-fluoro-propionic acid n-butyl ester | 0.83 | 13 | Colorless, resinous | 60.0 (60.2) | 7.1 (6.9) | 22.3 (21.9) |
| Preparation Example 3 (Compound No. 3) | 2-(3',5'-dimethyl-phenoxy)-1-methyl-ethyl biganide | $\alpha$-chloro propionic acid methyl ester | 1.61 | 24 | Colorless, resinous | 56.2 (57.2) | 6.7 (6.6) | 21.2 (20.9) |

TABLE 1-continued

| Preparation Example No. (Compound No.) | Starting Materials I | Starting Materials II | Yield (g) | Yield (%) | Melting Point (°C.) | Elementary Analysis (%) C | H | N |
|---|---|---|---|---|---|---|---|---|
| Preparation Example 4 (Compound No. 4) | 2-(2',3'-dimethyl-phenoxy)-1-methyl-ethyl biganide | α-fluoro, α-methyl propionic acid ethyl ester | 2.80 | 42 | 134.5–136.0 | 60.9 (61.2) | 7.1 (7.3) | 21.2 (21.0) |
| Preparation Example 5 (Compound No. 5) | 2-(2',5'-dimethyl-phenoxy)-1-methyl-ethyl biganide | α-fluoro, α-methyl propionic acid ethyl ester | 2.27 | 34 | Colorless, resinous | 63.0 (61.2) | 7.4 (7.3) | 21.1 (21.0) |
| Preparation Example 6 (Compound No. 6) | 2-(2',5'-dimethyl-phenoxy)-1-methyl-ethyl biganide | α-chloro, α-methyl propionic acid ethyl ester | 1.06 | 15 | Colorless, resinous | 59.0 (58.4) | 6.7 (6.9) | 20.4 (20.0) |
| Preparation Example 7 (Compound No. 7) | 2-(2', 3'-dimethyl-phenoxy)-1-methyl-ethyl biganide | α-chloro, α-methyl propionic acid ethyl ester | 0.82 | 12 | Colorless, resinous | 58.0 (58.4) | 7.2 (6.9) | 19.6 (20.0) |
| Preparation Example 8 (Compound No. 8) | 2-(2',3'-dimethyl-phenoxy)-1-methyl-ethyl biganide | α-fluoro-propionic acid n-butyl ester | 0.48 | 8 | Colorless, resinous | 60.0 (60.2) | 6.9 (6.9) | 22.3 (21.9) |
| Preparation Example 9 (Compound No. 9) | 2-(3',5'-dimethyl-phenoxy)-1-methyl-ethyl biganide | α-chloro, α-methyl propionic acid ethyl ester | 2.01 | 29 | Colorless, resinous | 57.9 (58.4) | 7.0 (6.9) | 20.2 (20.0) |
| Preparation Example 10 (Compound No. 10) | 2-(3',5'-dimethyl-phenoxy)-1-methyl-ethyl biganide | α-bromo, α-methyl propionic acid ethyl ester | 1.85 | 24 | Colorless, resinous | 52.2 (51.8) | 6.0 (6.1) | 17.5 (17.8) |
| Preparation Example 11 (Compound No. 11) | 2-(3'-trifluoro-methylphenoxy)-1-methyl-ethyl biganide | α-fluoro, α-methyl propionic acid ethyl ester | 2.09 | 28 | Colorless, resinous | 51.9 (51.5) | 5.0 (5.1) | 18.4 (18.8) |
| Preparation Example 12 (Compound No. 12) | 2-(3'-methyl-phenoxy)-1-methyl ethyl biganide | α-fluoro, α-methyl propionic acid ethyl ester | 1.32 | 21 | 95.3–97.0 | 60.0 (60.2) | 6.8 (6.9) | 22.2 (21.9) |
| Preparation Example 13 (Compound No. 13) | 2-(3'-methyl-phenoxy)-1-methyl ethyl biganide | α-fluoro-propionic acid n-butyl ester | 0.45 | 7 | Colorless, resinous | 59.2 (59.0) | 6.9 (6.6) | 22.5 (22.9) |
| Preparation Example 14 (Compound No. 14) | 2-(3'-trifluoro-methylphenoxy)-1-methyl-ethyl biganide | α-fluoro-propionic acid n-butyl ester | 1.09 | 15 | Colorless, resinous | 50.5 (50.1) | 4.5 (4.8) | 19.9 (19.5) |
| Preparation Example 15 (Compound No. 15) | 2-(3'-methyl-phenoxy)-1-methyl ethyl biganide | α-chloro, α-methyl propionic acid ethyl ester | 1.11 | 16 | Colorless, resinous | 57.0 (57.2) | 6.9 (6.6) | 20.5 (20.9) |
| Preparation Example 16 (Compound No. 16) | 2-phenoxy 1-methyl-ethyl biganide | α-chloro, α-methyl propionic acid ethyl ester | 1.04 | 16 | Colorless, resinous | 56.4 (56.0) | 6.1 (6.3) | 22.0 (21.8) |
| Preparation Example 17 (Compound No. 17) | 2-phenoxy 1-methyl-ethyl biganide | α-fluoro, α-methyl propionic acid ethyl ester | 1.64 | 27 | Colorless, resinous | 58.7 (59.0) | 6.8 (6.6) | 23.1 (22.9) |
| Preparation Example 18 (Compound No. 18) | 2-phenoxy 1-methyl-ethyl biganide | α-fluoro-propionic acid n-butyl ester | 0.58 | 9.6 | Colorless, resinous | 58.1 (57.7) | 6.0 (6.1) | 24.2 (24.0) |
| Preparation Example 19 (Compound No. 19) | 2-(3'-methoxy-phenoxy)-1-methyl-ethyl biganide | α-fluoro, α-methyl propionic acid ethyl ester | 1.42 | 21 | Colorless, resinous | 56.9 (57.3) | 6.8 (6.6) | 20.7 (20.9) |
| Preparation Example 20 (Compound No. 20) | 2-(3',4'-dimethyl-phenoxy)-1-methyl-ethyl biganide | α-fluoro, α-methyl propionic acid ethyl ester | 0.61 | 9.2 | Colorless, resinous | 60.8 (61.2) | 6.9 (7.3) | 21.3 (21.0) |
| Preparation Example 21 (Compound No. 21) | 2-(3'-fluoro-phenoxy)-1-methyl-ethyl biganide | α-fluoro, α-methyl propionic acid ethyl ester | 3.88 | 60 | Colorless, resinous | 55.9 (55.7) | 5.6 (5.9) | 22.0 (21.7) |
| Preparation Example 22 (Compound No. 22) | 2-(2'-fluoro-phenoxy)-1-methyl ethyl biganide | α-fluoro, α-methyl propionic acid ethyl ester | 0.19 | 3 | Colorless, resinous | 56.0 (55.7) | 6.2 (5.9) | 21.5 (21.7) |
| Preparation | 2-(4'-fluoro- | α-fluoro, α-methyl | 0.84 | 13 | Color- | 55.2 | 5.8 | 21.6 |

TABLE 1-continued

| Preparation Example No. (Compound No.) | Starting Materials I | Starting Materials II | Yield (g) | Yield (%) | Melting Point (°C.) | C | H | N |
|---|---|---|---|---|---|---|---|---|
| Example 23 (Compound No. 23) | phenoxy)-1-methyl-ethyl biganide | propionic acid ethyl ester | | | less, resinous | (55.7) | (5.9) | (21.7) |
| Preparation Example 24 (Compound No. 24) | 1-(benzofuran-2'-yl) ethyl biganide | α-fluoro, α-methyl propionic acid ethyl ester | 4.74 | 75 | 161.5–162.4 | 60.7 (60.9) | 5.9 (5.8) | 22.5 (22.2) |
| Preparation Example 25 (Compound No. 25) | 1-(benzofuran-2'-yl) ethyl biganide | α-chloro, α-methyl propionic acid methyl ester | 5.64 | 85 | 138.8–139.7 | 57.5 (57.9) | 5.2 (5.5) | 20.8 (21.1) |
| Preparation Example 26 (Compound No. 26) | 1-(benzofuran-2'-yl) ethyl biganide | α-bromo, α-methyl propionic acid ethyl ester | 5.56 | 74 | 149.8–150.7 | 51.3 (51.1) | 4.6 (4.8) | 18.3 (18.6) |
| Preparation Example 27 (Compound No. 27) | 1-(benzofuran-2'-yl) ethyl biganide | α-fluoro-propionic acid ethyl ester | 2.84 | 47 | 139.0–140.2 | 59.6 (59.8) | 5.1 (5.4) | 23.5 (23.2) |
| Preparation Example 28 (Compound No. 28) | 1-(benzofuran-2'-yl) ethyl biganide | α-chloro-propionic acid methyl ester | 5.02 | 79 | 145.3–147.4 | 56.5 (56.7) | 5.3 (5.1) | 22.3 (22.0) |
| Preparation Example 29 (Compound No. 29) | 1-(benzofuran-2'-yl) ethyl biganide | α-fluoro-α-methyl butyric acid methyl ester | 3.20 | 48 | 153.9–155.2 | 62.2 (62.0) | 6.4 (6.1) | 21.1 (21.3) |
| Preparation Example 30 (Compound No. 30) | 1-(benzothiophen 2'-yl) ethyl biganide | α-fluoro, α-methyl propionic acid ethyl ester | 4.76 | 72 | 134.2–136.0 | 58.2 (58.0) | 5.3 (5.5) | 20.9 (21.1) |
| Preparation Example 31 (Compound No. 31) | 1-(benzothiophen 2'-yl) ethyl biganide | α-chloro, α-methyl propionic acid methyl ester | 4.86 | 70 | Colorless, resinous | 55.0 (55.2) | 5.4 (5.2) | 20.3 (20.1) |
| Preparation Example 32 (Compound No. 32) | 1-(benzothiophen 2'-yl) ethyl biganide | α-fluoro-propionic acid ethyl ester | 2.28 | 36 | Colorless, resinous | 57.0 (56.8) | 4.9 (5.1) | 22.5 (22.1) |
| Preparation Example 33 (Compound No. 33) | 1-(6'-methyl-benzofuran-2'-yl) ethyl biganide hydrochloride | α-fluoro, α-methyl propionic acid ethyl ester | 5.54 | 84 | 168.5–169.3 | 62.4 (62.0) | 6.0 (6.1) | 21.1 (21.3) |
| Preparation Example 34 (Compound No. 34) | 1-(6'-methyl-benzofuran-2'-yl) ethyl biganide hydrochloride | α-fluoro-propionic acid ethyl ester | 3.28 | 52 | Colorless resinous | 61.2 (60.9) | 5.6 (5.8) | 22.0 (22.2) |
| Preparation Example 35 (Compound No. 35) | 1-(6'-methyl-benzofuran-2'-yl) ethyl biganide hydrochloride | α-chloro, α-methyl propionic acid methyl ester | 5.18 | 75 | Colorless, resinous | 58.7 (59.0) | 5.8 (5.8) | 20.4 (20.3) |
| Preparation Example 36 (Compound No. 36) | 2-(3'-methoxy, 4'-methylphenyl)-1-methyl-ethyl biganide hydrochloride | α-fluoro, α-methyl propionic acid ethyl ester | 2.17 | 34 | 115.1–116.8 | 58.7 (60.2) | 6.7 (6.9) | 21.6 (21.9) |
| Preparation Example 37 (Compound No. 37) | 2-(3'-methoxy, 4'-methylphenyl)-1-methyl-ethyl biganide hydrochloride | α-fluoro-propionic acid n-butyl ester | 1.34 | 22 | Colorless, resinous | 57.3 (59.0) | 6.5 (6.6) | 22.8 (22.9) |
| Preparation Example 38 (Compound No. 38) | 2-(3'-methoxy, 4'-methylphenyl)-1-methyl-ethyl biganide hydrochloride | α-chloro, α-methyl propionic acid ethyl ester | 2.42 | 36 | Colorless, resinous | 57.4 (57.2) | 6.7 (6.6) | 20.6 (20.9) |
| Preparation Example 39 (Compound No. 39) | 2-(3'-methyl, 4'-methoxyphenyl)-1-methyl-ethyl biganide hydrochloride | α-fluoro, α-methyl propionic acid ethyl ester | 1.98 | 31 | Colorless resinous | 60.3 (60.2) | 6.8 (6.9) | 22.2 (21.9) |
| Preparation Example 40 (Compound No. 40) | 2-(3'-methyl, 4'-methoxyphenyl)-1-methyl-ethyl biganide hydrochloride | α-fluoro-propionic acid n-butyl ester | 1.22 | 20 | Colorless, resinous | 59.1 (59.0) | 6.9 (6.6) | 22.7 (22.9) |
| Preparation | 2-(3'-methyl, 4'- | α-chloro, α-methyl | 2.22 | 33 | Color- | 57.0 | 6.8 | 21.0 |

TABLE 1-continued

| Preparation Example No. (Compound No.) | Starting Materials | | Yield (g) | Yield (%) | Melting Point (°C.) | Results of Analysis (%) Elementary Analysis (%) | | |
|---|---|---|---|---|---|---|---|---|
| | I | II | | | | C | H | N |
| Example 41 (Compound No. 41) | methoxyphenyl)-1-methyl-ethyl biganide hydrochloride | propionic acid ethyl ester | | | less, resinous | (57.2) | (6.6) | (20.9) |

*The value in the brackets show the theoretical value.

TABLE 2

| No. | Structural formula of triazine derivative | Molecular weight of triazine derivative | Triazine derivative |
|---|---|---|---|
| Preparation Example 1 | | $C_{17}H_{24}N_5OF$ 333.4 | 2-amino-4-(α-fluoro, α-methyl ethyl)-6-[2-(3',5'-dimethylphenoxy)-1-methyl-ethylamino]-s-triazine |
| Preparation Example 2 | | $C_{16}H_{22}N_5OF$ 319.4 | 2-amino-4-(α-fluoroethyl)-6-[2-(3',5'-dimethylphenoxy)-1-methyl-ethylamino]-s-triazine |
| Preparation Example 3 | | $C_{16}H_{22}N_5OCl$ 335.8 | 2-amino-4-(α-chloroethyl)-6-[2-(3',5'-dimethylphenoxy)-1-methyl-ethylamino]-s-triazine |
| Preparation Example 4 | | $C_{17}H_{24}N_5OF$ 333.4 | 2-amino-4-(α-fluoro, α-methyl ethyl)-6-[2-(2',3'-dimethylphenoxy)-1-methyl-ethylamino]-s-triazine |
| Preparation Example 5 | | $C_{17}H_{24}N_5OF$ 333.4 | 2-amino-4-(α-fluoro, α-methyl ethyl)-6-[2-(2',5'-dimethylphenoxy)-1-methyl-ethylamino]-s-triazine |

TABLE 2-continued

| No. | Structural formula of triazine derivative | Molecular weight of triazine derivative | Triazine derivative |
|---|---|---|---|
| Preparation Example 6 | (2,5-dimethylphenyl)-OCH₂CH(CH₃)-NH-[triazine with C(CH₃)₂Cl substituent]-NH₂ | $C_{17}H_{24}N_5OCl$ 349.9 | 2-amino-4-(α-chloro, α-methyl ethyl)-6-[2-(2',5'-dimethyl-phenoxy)-1-methyl-ethylamino]-s-triazine |
| Preparation Example 7 | (2,3-dimethylphenyl)-OCH₂CH(CH₃)-NH-[triazine with C(CH₃)₂Cl substituent]-NH₂ | $C_{17}H_{24}N_5OCl$ 349.9 | 2-amino-4-(α-chloro, α-methyl ethyl)-6-[2-(2',3'-dimethyl-phenoxy)-1-methyl-ethylamino]-s-triazine |
| Preparation Example 8 | (2,3-dimethylphenyl)-OCH₂CH(CH₃)-NH-[triazine with CH(CH₃)F substituent]-NH₂ | $C_{16}H_{22}N_5OF$ 319.4 | 2-amino-4-(α-fluoroethyl)-6-[2-(2',3'-dimethylphenoxy)-1-methyl-ethylamino]-s-triazine |
| Preparation Example 9 | (3,5-dimethylphenyl)-OCH₂CH(CH₃)-NH-[triazine with C(CH₃)₂Cl substituent]-NH₂ | $C_{17}H_{24}N_5OCl$ 349.9 | 2-amino-4-(α-chloro, α-methyl ethyl)-6-[2-(3',5'-dimethyl-phenoxy)-1-methyl-ethylamino]-s-triazine |
| Preparation Example 10 | (3,5-dimethylphenyl)-O-CH₂CH(CH₃)-NH-[triazine with C(CH₃)₂Br substituent]-NH₂ | $C_{17}H_{24}N_5OBr$ 394.3 | 2-amino-4-(α-bromo, α-methyl ethyl)-6-[2-(3',5'-dimethyl-phenoxy)-1-methyl-ethylamino]-s-triazine |
| Preparation Example 11 | (3-trifluoromethylphenyl)-OCH₂CH(CH₃)-NH-[triazine with C(CH₃)₂F substituent]-NH₂ | $C_{16}H_{19}N_5OF_4$ 373.4 | 2-amino-4-(α-fluoro, α-methyl ethyl)-6-[2-(3'-trifluoro-methylphenoxy)-1-methyl-ethyl-amino]-s-triazine |
| Preparation Example 12 | (3-methylphenyl)-OCH₂CH(CH₃)-NH-[triazine with C(CH₃)₂F substituent]-NH₂ | $C_{16}H_{22}N_5OF$ 319.4 | 2-amino-4-(α-fluoro, α-methyl ethyl)-6-[2-(3'-methylphenoxy)-1-methyl-ethylamino]-s-triazine |

TABLE 2-continued

| No. | Structural formula of triazine derivative | Molecular weight of triazine derivative | Triazine derivative |
|---|---|---|---|
| Preparation Example 13 | (3-methylphenyl)-O-CH₂CH(CH₃)-NH-[triazine with NH₂, substituted by CH(CH₃)F] | C₁₅H₂₀N₅OF 305.4 | 2-amino-4-(α-fluoroethyl)-6-[2-(3'-methylphenoxy)-1-methyl-ethylamino]-s-triazine |
| Preparation Example 14 | (3-trifluoromethylphenyl)-O-CH₂CH(CH₃)-NH-[triazine with NH₂, substituted by CH(CH₃)F] | C₁₅H₁₇N₅OF₄ 359.3 | 2-amino-4-(α-fluoroethyl)-6-[2-(3'-trifluoromethylphenoxy)-1-methyl-ethylamino]-s-triazine |
| Preparation Example 15 | (3-methylphenyl)-O-CH₂CH(CH₃)-NH-[triazine with NH₂, substituted by C(CH₃)₂Cl] | C₁₆H₂₂N₅OCl 335.8 | 2-amino-4-(α-chloro, α-methyl ethyl)-6-[2-(3'-methylphenoxy)-1-methyl-ethylamino]-s-triazine |
| Preparation Example 16 | phenyl-O-CH₂CH(CH₃)-NH-[triazine with NH₂, substituted by C(CH₃)₂Cl] | C₁₅H₂₀N₅OCl 321.8 | 2-amino-4-(α-chloro, α-methyl ethyl)-6-(2-phenoxy)-1-methyl-ethylamino)-s-triazine |
| Preparation Example 17 | phenyl-O-CH₂CH(CH₃)-NH-[triazine with NH₂, substituted by C(CH₃)₂F] | C₁₅H₂₀N₅OF 305.4 | 2-amino-4-(α-fluoro, α-methyl ethyl)-6-(2-phenoxy)-1-methyl-ethylamino)-s-triazine |
| Preparation Example 18 | phenyl-O-CH₂CH(CH₃)-NH-[triazine with NH₂, substituted by CH(CH₃)F] | C₁₄H₁₈N₅OF 291.3 | 2-amino-4-(α-fluoroethyl)-6-(2-phenoxy-1-methyl-ethylamino)-s-triazine |
| Preparation Example 19 | (3-methoxyphenyl)-O-CH₂CH(CH₃)-NH-[triazine with NH₂, substituted by C(CH₃)₂F] | C₁₆H₂₂N₅O₂F 335.4 | 2-amino-4-(α-fluoro, α-methyl ethyl)-6-[2-(3'-methoxyphenoxy)-1-methyl-ethylamino]-s-triazine |
| Preparation Example 20 | (3,4-dimethylphenyl)-O-CH₂CH(CH₃)-NH-[triazine with NH₂, substituted by C(CH₃)₂F] | C₁₇H₂₄N₅OF 333.4 | 2-amino-4-(α-fluoro, α-methyl ethyl)-6-[2-(3',4'-dimethylphenoxy)-1-methyl-ethylamino]-s-triazine |

TABLE 2-continued

| No. | Structural formula of triazine derivative | Molecular weight of triazine derivative | Triazine derivative |
|---|---|---|---|
| Preparation Example 21 | | $C_{15}H_{19}N_5OF_2$ 323.3 | 2-amino-4-(α-fluoro, α-methyl ethyl)-6-[2-(3'-fluorophenoxy)-1-methyl-ethylamino]-s-triazine |
| Preparation Example 22 | | $C_{15}H_{19}N_5OF_2$ 323.3 | 2-amino-4-(α-fluoro, α-methyl ethyl)-6-[2-(2'-fluorophenoxy)-1-methyl-ethylamino]-s-triazine |
| Preparation Example 23 | | $C_{15}H_{19}N_5OF_2$ 323.3 | 2-amino-4-(α-fluoro, α-methyl ethyl)-6-[2-(4'-fluorophenoxy)-1-methyl-ethylamino]-s-triazine |
| Preparation Example 24 | | $C_{16}H_{18}N_5OF$ 315.4 | 2-amino-4-[1-(benzofuran-2'-yl)ethylamino]-6-(α-fluoro, α-methyl ethyl)-s-triazine |
| Preparation Example 25 | | $C_{16}H_{18}N_5OCl$ 331.8 | 2-amino-4-[1-(benzofuran-2'-yl)ethylamino]-6-(α-chloro, α-methyl ethyl)-s-triazine |
| Preparation Example 26 | | $C_{16}H_{18}N_5OBr$ 376.3 | 2-amino-4-[1-(benzofuran-2'-yl)ethylamino]-6-(α-bromo, α-methyl ethyl)-s-triazine |
| Preparation Example 27 | | $C_{15}H_{16}N_5OF$ 301.3 | 2-amino-4-[1-(benzofuran-2'-yl)ethylamino]-6-(α-fluoroethyl)-s-triazine |
| Preparation Example 28 | | $C_{15}H_{16}N_5OCl$ 317.8 | 2-amino-4-[1-(benzofuran-2'-yl)ethylamino]-6-(α-chloroethyl)-s-triazine |

TABLE 2-continued

| No. | Structural formula of triazine derivative | Molecular weight of triazine derivative | Triazine derivative |
|---|---|---|---|
| Preparation Example 29 | | $C_{17}H_{20}N_5OF$ 329.4 | 2-amino-4-[1-(benzofuran-2'-yl)ethylamino]-6-(α-fluoro, α-methyl propyl)-s-triazine |
| Preparation Example 30 | | $C_{16}H_{18}N_5SF$ 331.4 | 2-amino-4-[1-(benzothiophen-2'-yl)ethylamino]-6-(α-fluoro, α-methyl propyl)-s-triazine |
| Preparation Example 31 | | $C_{16}H_{18}N_5SCl$ 347.9 | 2-amino-4-[1-(benzothiophen-2'-yl)ethylamino]-6-(α-chloro, α-methyl ethyl)-s-triazine |
| Preparation Example 32 | | $C_{15}H_{16}N_5SF$ 317.4 | 2-amino-4-[1-(benzothiophen-2'-yl)ethylamino]-6-(α-fluoroethyl)-s-triazine |
| Preparation Example 33 | | $C_{17}H_{20}N_5OF$ 329.4 | 2-amino-4-[1-(6'-methylbenzofuran-2'-yl)ethylamino]-6-(α-fluoro, α-methyl ethyl)-s-triazine |
| Preparation Example 34 | | $C_{16}H_{18}N_5OF$ 315.4 | 2-amino-4-[1-(6'-methylbenzofuran-2'-yl)ethylamino]-6-(α-fluoroethyl)-s-triazine |
| Preparation Example 35 | | $C_{17}H_{20}N_5OCl$ 345.8 | 2-amino-4-[1-6'-methylbenzofuran-2'-yl)ethylamino]-6-(α-chloro, α-methyl ethyl)-s-triazine |
| Preparation Example 36 | | $C_{18}H_{22}N_5OF$ 319.4 | 2-amino-4-(α-fluoro, α-methyl ethyl)-6-[2-(3'-methyloxy, 4'-methylphenyl)-1-methyl-ethylamino]-s-triazine |

TABLE 2-continued

| No. | Structural formula of triazine derivative | Molecular weight of triazine derivative | Triazine derivative |
|---|---|---|---|
| Preparation Example 37 | (structure) | $C_{15}H_{20}N_5OF$ 305.4 | 2-amino-4-(α-fluoroethyl)-6-[2-(3'-methoxy, 4'-methylphenyl)-1-methyl-ethylamino]-s-triazine |
| Preparation Example 38 | (structure) | $C_{18}H_{22}N_5OCl$ 335.8 | 2-amino-4-(α-chloro, α-methyl)-6-[2-(3'-methoxy, 4'-methylphenyl)-1-methyl-ethylamino]-s-triazine |
| Preparation Example 39 | (structure) | $C_{16}H_{22}N_5OF$ 319.4 | 2-amino-4-(α-fluoro, α-methyl ethyl)-6-[2-(3'-methyl, 4'-methoxyphenyl)-1-methyl-ethylamino]-s-triazine |
| Preparation Example 40 | (structure) | $C_{15}H_{20}N_5OF$ 305.4 | 2-amino-4-(α-fluoroethyl-6-[2-(3'-methyl, 4'-methoxyphenyl)-1-methyl-ethylamino]-s-triazine |
| Preparation Example 41 | (structure) | $C_{16}H_{22}N_5OCl$ 335.8 | 2-amino-4-(α-fluoro, α-methylethyl)-6-[2-(3'-methyl, 4'-methoxyphenyl)-1-methyl-ethylamino]-s-triazine |

TABLE 3

| Preparation Example No. | Compound prepared | Infrared absorption[*1] spectrum (cm$^{-1}$) | Proton nuclear magnetic resonance spectrum[*2] (ppm) |
|---|---|---|---|
| 1 | Compound 1 | 3470, 3350, 3280 1660, 1620, 1560 | 1.35(3H, d), 1.65(6H, d), 2.28(6H, s), 3.91~3.99(2H, m), 4.25~4.70(1H, brs), 5.44~5.80(3H, brs), 6.55~6.60(3H, m) solvent: deuterated chloroform |
| 2 | Compound 2 | 3500, 3440, 3200 1660, 1620, 1560 | 1.33(3H, d), 1.60(3H, q), 2.26(6H, s), 3.90~4.03(2H, m), 4.30~4.63(1H, brs), 4.80~5.14(1H, m), 5.38~5.77(3H, m), 6.52~6.60(3H, m) solvent: deuterated chloroform |
| 3 | Compound 3 | 3500, 3420, 3330 1660, 1620, 1560 | 1.32(3H, d), 1.70(3H, d), 2.23(6H, s), 3.80~4.18(2H, m), 4.32~4.80(3H, m), 6.50~6.60(4H, brs) solvent: deuterated acetone |
| 4 | Compound 4 | 3510, 3350, 3200 1660, 1620, 1560 | 1.38(3H, d), 1.55(3H, d), 2.10(3H, s), 2.23(3H, s), 3.80~4.21(2H, m), 4.30~4.78(2H, brs), 6.18~7.42(6H, brs) solvent: deuterated acetone |
| 5 | Compound 5 | 3470, 3350, 3250 1658, 1586, 1540 | 1.37(3H, d), 1.63(6H, d), 2.17(3H, s), 2.30(3H, s), 3.96~4.00(2H, m), 4.32~4.78(1H, brs), 5.26~5.73(3H, brs), 6.62~7.35(3H, m) solvent: deuterated chloroform |
| 6 | Compound 6 | 3530, 3360, 3250 1650, 1580, 1575 | 1.40(3H, d), 1.88(6H, s), 2.19(3H, s), 2.31(3H, s), 3.96~4.03(2H, m), 4.32~4.80(1H, brs), 5.32~5.92(3H, brs), 6.54~7.22(3H, m) solvent: deuterated chloroform |
| 7 | Compound 7 | 3500, 3350, 3200 1650, 1590, 1560 | 1.39(3H, d), 1.88(6H, s), 2.16(3H, s), 2.27(3H, s), 3.91~4.01(2H, m), 4.28~4.82(1H, brs), 5.28~5.88(3H, brs), 6.64~7.29(3H, m) solvent: deuterated chloroform |
| 8 | Compound 8 | 3530, 3360, 3220 1660, 1580, 1560 | 1.38(3H, d), 1.62(3H, q), 2.14(3H, s), 2.28(3H, s), 3.95~4.00(2H, m), 4.32~4.75(1H, brs), 4.87~5.57(4H, brs), |

TABLE 3-continued

| Preparation Example No. | Compound prepared | Infrared absorption*1 spectrum (cm$^{-1}$) | Proton nuclear magnetic resonance spectrum*2 (ppm) |
|---|---|---|---|
| 9 | Compound 9 | 3460, 3350, 3200 1660, 1620, 1550 | 6.64~7.20(3H, m) solvent: deuterated chloroform 1.35(3H, d), 1.89(6H, s), 2.30(6H, s), 3.88~4.05(2H, m), 4.24~4.72(1H, brs), 5.16~5.77(3H, brs), 6.42~6.79(3H, m) solvent: deuterated chloroform |
| 10 | Compound 10 | 3500, 3360, 3200 1640, 1600, 1560 | 1.37(3H, d), 2.08(6H, s), 2.29(6H, s), 3.84~4.07(2H, m), 4.26~4.77(1H, brs), 5.08~5.77(3H, brs), 6.44~6.75(3H, m) solvent: deuterated chloroform |
| 11 | Compound 11 | 3530, 3360, 3200 1600, 1580, 1560 | 1.37(3H, d), 1.63(6H, d), 3.93~4.09(2H, m), 4.27~4.72 (1H, brs), 5.52~6.60(3H, brs), 7.02~7.48(4H, m) solvent: deuterated chloroform |
| 12 | Compound 12 | 3440, 3330 1650, 1610, 1570 | 1.36(3H, d), 1.64(6H, d), 2.32(3H, s), 3.94~4.01(2H, m), 4.29~4.65(1H, brs), 5.28~5.90(3H, brs), 6.74~7.17(4H, m) solvent: deuterated chloroform |
| 13 | Compound 13 | 3500, 3340, 3190 1640, 1620, 1564 | 1.36(3H, d), 1.62(3H, q), 2.32(3H, s), 3.94~4.00(2H, m), 4.19~4.70(1H, brs), 4.96(1H, q), 5.17~5.99(3H, brs), 6.68~7.24(4H, m) solvent: deuterated chloroform |
| 14 | Compound 14 | 3500, 3350, 3200 1640, 1600, 1560 | 1.36(3H, d), 1.62(3H, q), 3.98~4.08(2H, m), 4.29~4.70 (1H, brs), 4.97(1H, q), 5.39~6.50(3H, brs) solvent: deuterated chloroform |
| 15 | Compound 15 | 3500, 3350, 3230 1655, 1600, 1575 | 1.35(3H, d), 1.88(6H, s), 2.32(3H, s), 3.94~4.01(2H, m), 4.23~4.77(1H, brs), 5.09~5.99(3H, brs), 6.68~7.16(4H, m) solvent: deuterated chloroform |
| 16 | Compound 16 | 3500, 3360, 3220 1655, 1600, 1460 | 1.33(3H, d), 1.89(6H, s), 3.97~4.04(2H, m), 4.26~4.76 (1H, brs), 4.96~5.73(3H, brs), 6.87~7.38(5H, m) solvent: deuterated chloroform |
| 17 | Compound 17 | 3500, 3380, 3180 1650, 1600, 1560 | 1.34(3H, d), 1.63(6H, d), 3.93~4.01(2H, m), 4.18~4.70 (1H, brs), 5.61~5.58(3H, brs), 6.84~7.38(5H, m) solvent: deuterated chloroform |
| 18 | Compound 18 | 3510, 3350, 3200 1660, 1610, 1560 | 1.34(3H, d), 1.60(3H, q), 3.88~4.00(2H, m), 4.25~4.73 (1H, brs), 4.95(1H, q), 5.38~6.62(3H, brs), 6.83~7.36 (5H, m) solvent: deuterated chloroform |
| 19 | Compound 19 | 3470, 3380, 3220 1650, 1610, 1575 | 1.36(3H, d), 1.64(6H, d), 3.79(3H, s), 3.91~4.04(2H, m), 4.28~4.65(1H, brs), 5.32~5.92(3H, brs), 6.48~7.17(4H, m) solvent: deuterated chloroform |
| 20 | Compound 20 | 3440, 3330, 3200 1650, 1595, 1560 | 1.33(3H, d), 1.62(6H, d), 2.17(3H, s), 2.21(3H, s), 3.89~ 3.96(2H, m), 4.20~4.67(1H, brs), 5.48~6.48(3H, brs), 6.57~7.12(3H, m) solvent: deuterated chloroform |
| 21 | Compound 20 | 3440, 3330, 3240 1640, 1585, 1560 | 1.35(3H, d), 1.64(6H, d), 3.93~4.03(2H, m), 4.26~4.67 (1H, brs), 5.22~5.92(3H, brs), 6.59~7.37(4H, m) solvent: deuterated chloroform |
| 22 | Compound 22 | 3500, 3320, 3240 1650, 1600, 1570 | 1.39(3H, d), 1.64(6H, d), 4.01~4.10(2H, m), 4.29~4.72 (1H, brs), 5.07~5.74(3H, brs), 6.99~7.02(4H, m) solvent: deuterated chloroform |
| 23 | Compound 23 | 3520, 3350, 3220 1660, 1600, 1560 | 1.36(3H, d), 1.64(6H, d), 3.91~3.99(2H, m), 4.23~4.74 (1H, brs), 5.13~5.68(3H, brs), 6.86~6.98(4H, m) solvent: deuterated chloroform |
| 24 | Compound 24 | 3500, 3310, 3220 1660, 1600, 1540 | 1.56(6H, d), 1.65(3H, d), 5.30~5.71(1H, m), 6.20~6.59 (2H, brs), 6.69(1H, s), 7.12~7.64(4H, m) solvent: deuterated acetone |
| 25 | Compound 25 | 3490, 3340, 3270 1640, 1610, 1560 | 1.62(3H, d), 1.89(6H, s), 5.25~5.78(1H, m), 6.57(1H, s), 7.11~7.56(4H, m) solvent: deuterated acetone |
| 26 | Compound 26 | 3490, 3350 1650, 1580, 1560 | 1.63(3H, d), 2.07(6H, s), 5.24~5.77(1H, m), 6.57(1H, s), 7.16~7.58(4H, m) solvent: deuterated acetone |
| 27 | Compound 27 | 3490, 3320, 3190 1650, 1600, 1540 | 1.60(3H, d, d), 1.61(3H, d), 4.90~5.42(1H, q, q), 5.40~6.08 (1H, brs), 6.69(1H, s), 7.11~7.56(4H, m) solvent: deuterated acetone |
| 28 | Compound 28 | 3490, 3320, 3220 1660, 1600, 1560 | 1.57(3H, d), 1.72(3H, d), 4.69(1H, q), 5.24~5.73(1H, m), 6.69(1H, s), 7.08~7.68(4H, m) solvent: deuterated acetone |
| 29 | Compound 29 | 3460, 3320, 3180 1650, 1590, 1540 | 1.20(3H, t), 1.57(3H, d), 1.65(3H, d), 1.88(1H, q), 5.16~ 6.00(4H, brs), 6.57(1H, s), 7.10~7.56(4H, m) solvent: deuterated acetone |
| 30 | Compound 30 | 3540, 3290, 3150 1660, 1620, 1560 | 1.61(6H, d), 1.62(3H, d), 5.31~6.42(4H, brs), 7.08~7.83 (5H, m) solvent: deuterated chloroform |
| 31 | Compound 31 | 3520, 3430, 3360 1650, 1570 | 1.57(3H, d), 1.87(6H, s), 5.26~6.33(4H, brs), 6.99~7.76 (5H, m) solvent: deuterated chloroform |
| 32 | Compound 32 | 3500, 3430, 3330 1650, 1570 | 1.53(3H, d, ), 1.62(3H, d), 4.69~5.88(3H, brs), 6.20~7.19 (3H, brs), 7.21~7.96(5H, m) solvent: deuterated acetone |
| 33 | Compound 33 | 3510, 3430, 3350 1660, 1570 | 1.58(6H, d), 1.62(3H, d), 2.41(3H, s), 5.22~5.67(1H, m), 6.28~6.92(3H, brs), 6.61(1H, s), 6.92~7.49(3H, m) solvent: deuterated acetone |
| 34 | Compound 34 | 3490, 3430, 3330 1650, 1570 | 1.60(3H, d, d), 1.62(3H, d), 2.42(3H, s), 4.72~5.85(5H, brs), 6.51(1H, s), 6.90~7.49(3H, m) solvent: deuterated chloroform |
| 35 | Compound 35 | 3500, 3430, 3350 1640, 1560 | 1.62(3H, d), 1.89(6H, s), 2.43(3H, s), 5.08~5.69(4H, brs), 6.52(1H, s), 6.90~7.49(3H, m) solvent: deuterated chloroform |
| 36 | Compound 36 | 3510, 3350, 3210 1660, 1600, 1570 | 1.52(3H, d), 1.55(6H, d), 2.12(3H, s), 3.80(3H, s), 5.04~ 5.40(2H, m), 6.48(1H, brs), 6.78~7.20(3H, m) solvent: deuterated acetone |
| 37 | Compound 37 | 3480, 3400, 3370 | 1.50(3H, d), 1.58(3H, d, d), 2.16(3H, s), 3.78(3H, s), 5.33~ |

TABLE 3-continued

| Preparation Example No. | Compound prepared | Infrared absorption*1 spectrum (cm$^{-1}$) | Proton nuclear magnetic resonance spectrum*2 (ppm) |
|---|---|---|---|
| | | 1670, 1620, 1560 | 6.34(4H, m), 6.78~7.10(3H, m) solvent: deuterated chloroform |
| 38 | Compound 38 | 3510, 3440, 3350 1650, 1570 | 1.52(3H, d), 1.89(6H, s), 3.82(3H, s), 4.95~5.67(4H, brs), 6.76~7.30(3H, m) solvent: deuterated chloroform |
| 39 | Compound 39 | 3510, 3400, 3320 1640, 1560 | 1.42(3H, d), 1.60(6H, d), 2.19(3H, s), 3.79(3H, s), 4.88~5.29(1H, m), 5.61~7.20(3H, m) solvent: deuterated chloroform |
| 40 | Compound 40 | 3500, 3420, 3330 1650, 1570 | 1.47(3H, d), 1.56(3H, d, d), 2.19(3H, s), 3.79(3H, s), 4.72~6.57(5H, brs), 6.64~7.28(3H, m) solvent: deuterated chloroform |
| 41 | Compound 41 | 3510, 3420, 3350 1650, 1630, 1570 | 1.51(3H, d), 1.88(6H, s), 2.20(3H, s), 3.81(3H, s), 4.85~5.58(4H, brs), 6.69~7.29(3H, m) solvent: deuterated chloroform |

*1KBr tablet method
*2Internal standard: tetramethyl silane

In the following, the actual method for form preparation is described by way of formulation examples. In the formulation examples given below, "parts" refers to % by weight.

Formulation Example 1

Water-dispersible powder

| | |
|---|---|
| Compound of Preparation Example 1 | 20 parts |
| Diatomaceous earth | 62 parts |
| White carbon | 15 parts |
| Sodium alkylbenzene sulfonate | 2 parts |
| Sodium lignin sulfonate | 1 part |

The above were blended and uniformly mixed and pulverized to give 100 parts of a water-dispersible powder.

Formulation Example 2

Emulsion

| | |
|---|---|
| Compound of Preparation Example 2 | 40 parts |
| Xylene | 20 parts |
| Dimethyl formamide | 20 parts |
| Solpol 2806B (surface active agent, manufactured by Toho Chemical Industry) | 20 parts |

The above were uniformly dissolved and mixed to give 100 parts of an emulsion.

Formulation Example 3

Dust

| | |
|---|---|
| Compound of Preparation Example 3 | 2 parts |
| Diatomaceous earth | 20 parts |
| Talc | 78 parts |

The above were blended and uniformly mixed and pulverized to give 100 parts of a dust.

Formulation Example 4

Granules

| | |
|---|---|
| Compound of Preparation Example 4 | 1 part |
| Bentonite | 30 parts |
| Talc | 66 parts |
| Sodium lignin sulfonate | 3 parts |

The above were blended, uniformly mixed and pulverized and thoroughly kneaded with addition of water followed by granulation and drying to give 100 parts of granules.

Formulation Example 5

Flowable agent

| | |
|---|---|
| Compound of Preparation Example 5 | 25 parts |
| Methyl cellulose | 0.3 part |
| Colloidal silica | 1.5 parts |
| Sodium lignin sulfonate | 1 part |
| Polyoxyethylene nonylphenyl ether | 2 parts |
| Water | 70.2 parts |

The above were thoroughly mixed and dispersed and the slurry-like mixture was subjected to wet-process pulverization to give 100 parts of a stable flowable agent.

Formulation Example 6

Water-dispersible Powder

A carrier for water-dispersible powder was obtained by uniformly pulverizing and mixing 97 parts of clay (commercial product name: Zieglite, manufactured by Zieglite Kogyo) as a carrier, 1.5 parts of an alkylaryl sulfonic acid salt (commercial product name: Neopelex, manufactured by Kao Atlas Co.) as a surface active agent and 1.5 parts of a non-ionic type and anionic type surface active agent (commercial product name: Solpol 800A, manufactured by Toho Chemical Industry Co.).

A water-dispersible powder was obtained by uniformly pulverizing and mixing 90 parts of this carrier for water dispersible powder and 10 parts of the triazine derivative obtained in the above described Preparation Examples 1 to 5.

EXAMPLES 1 to 41

Upland Field Soil Treatment Test

Wagner pots of 1/2000 were filled with a soil of non-paddy field and seeds of *Digitaria sanguinalis, Alopecurus myosuroides, Abutilon theophrasti, Veronica persica, Viola arvensis, Polygonum persicaria, Amaranthus patulus, Galium sparium var. echinospermon*, wheat, barley, corn and grain sorghum were uniformly sowed in the surface layer.

Prior to the germination of the wheat, barley, corn, grain sorghum and weeds thereafter, the soil surface was uniformly treated with a specified volume of a diluted solution of the herbicide obtained in the above described Formulation Example 6 and the pots were kept standing in a greenhouse with periodical water sprinkling.

Table 4 shows the results of the investigations of the herbicidal effects and phytotoxicity to the wheat, barley, corn and grain sorghum after 30 days from the treatment with the herbicide solution. The dose was 25 to 100 g/10 ares calculated as the amount of the effective ingredient. The phytotoxicity to the wheat, barley, corn and grain sorghum and the herbicidal effects are expressed as shown below by measuring the respective air-dried weights.

| Extent of phytotoxicity | Phytotoxicity to wheat, barley, corn & grain sorgham (relative to untreated zone) |
| --- | --- |
| 0 | 100% |
| 1 | 61 to 99% |
| 2 | 21 to 60% |
| 3 | 11 to 20% |
| 4 | 1 to 10% |
| 5 | 0% |

| Degree of herbicidal effects | Herbicidal effects (relative to untreated zone) |
| --- | --- |
| 0 | 100% |
| 1 | 61 to 99% |
| 2 | 21 to 60% |
| 3 | 11 to 20% |
| 4 | 1 to 10% |
| 5 | 0% |

COMPARATIVE EXAMPLES 1 TO 6

The same procedure as in Example 1 was undertaken excepting the use of the triazine derivatives A to C (described in the official publication of Japanese Patent Kokai No. 63-264465), D (described in the official publication of Japanese Patent Kokai No. 63-51379), E (described in the official publication of Japanese Patent Kokai No. 63-146876) or F (described in the official publication of Japanese Patent Toku-Sai-Hyo No. 88/02368) expressed by the formulas given below in place of the triazine derivative prepared in Preparation Example 1, in Example 1. The results are shown in Table 4.

Triazine derivative A
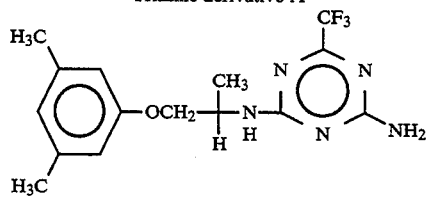

Triazine derivative B
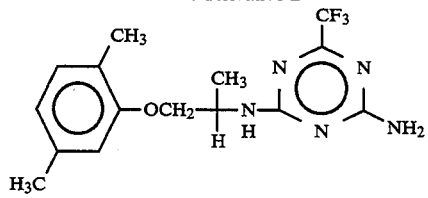

Triazine derivative C
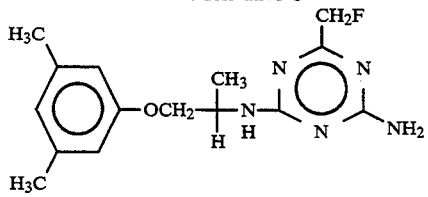

Triazine derivative D
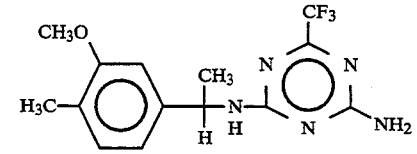

Triazine derivative E
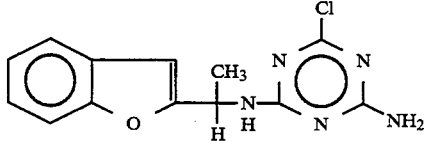

Triazine derivative F
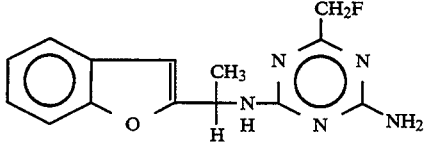

TABLE 4

| No. | Compound used | Amount of herbicide (g/10a) | Herbicidal effect | | | | | | | | | Phytotoxicity | | | |
|---|---|---|---|---|---|---|---|---|---|---|---|---|---|---|---|
| | | | Alopecurus myosuroides | Digitaria sanguinalis | Abutilon theophrasti | Veronica persica | Polygonum persicaria | Viola arvensis | Amaranthus patulus | Galium sparium var. echinospermon | Wheat | Barley | Corn | Grain sorghum |
| Example 1 | Compound of Preparation Example 1 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 2 | Compound of Preparation Example 2 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 3 | Compound of Preparation Example 3 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 4 | Compound of Preparation Example 4 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 5 | Compound of Preparation Example 5 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 6 | Compound of Preparation Example 6 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 7 | Compound of Preparation Example 7 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 8 | Compound of Preparation Example 8 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 9 | Compound of Preparation Example 9 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 10 | Compound of Preparation Example 10 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 11 | Compound of Preparation Example 11 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 12 | Compound of Preparation Example 12 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 13 | Compound of Preparation Example 13 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 14 | Compound of Preparation Example 14 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 15 | Compound of Preparation Example 15 | 100<br>50<br>25 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>5 | 0<br>0<br>0 | 0<br>0<br>0 | 0<br>0<br>0 | 0<br>0<br>0 |
| Example 16 | Compound of Preparation | 100<br>50 | 5<br>5 | 5<br>5 | 5<br>5 | 5<br>5 | 5<br>5 | 5<br>5 | 5<br>5 | 5<br>5 | 0<br>0 | 0<br>0 | 0<br>0 | 0<br>0 |

TABLE 4-continued

| No. | Compound used | Amount of herbicide (g/10a) | Herbicidal effect | | | | | | | | | Phytotoxicity | | | |
|---|---|---|---|---|---|---|---|---|---|---|---|---|---|---|---|
| | | | Alopecurus myosuroides | Digitaria sanguinalis | Abutilon theophrasti | Veronica persica | Polygonum persicaria | Viola arvensis | Amaranthus patulus | Galium sparium var. echinospermon | Wheat | Barley | Corn | Grain sorghum |
| Example 17 | Compound of Preparation Example 16 | 25 | 5 | 5 | 5 | 5 | 5 | 5 | 5 | 5 | 0 | 0 | 0 | 0 |
| | Compound of Preparation Example 17 | 100 | 5 | 5 | 5 | 5 | 5 | 5 | 5 | 5 | 0 | 0 | 0 | 0 |
| Example 18 | Compound of Preparation Example 18 | 50 | 5 | 5 | 5 | 5 | 5 | 5 | 5 | 0 | 0 | 0 | 0 | 0 |
| | | 25 | 5 | 5 | 5 | 5 | 5 | 5 | 5 | 5 | 0 | 0 | 0 | 0 |
| Example 19 | Compound of Preparation Example 19 | 100 | 5 | 5 | 5 | 5 | 5 | 5 | 5 | 5 | 0 | 0 | 0 | 0 |
| | | 50 | 5 | 5 | 5 | 5 | 5 | 5 | 5 | 5 | 0 | 0 | 0 | 0 |
| Example 20 | Compound of Preparation Example 20 | 25 | 5 | 5 | 5 | 5 | 5 | 5 | 5 | 5 | 0 | 0 | 0 | 0 |
| | | 100 | 5 | 5 | 5 | 5 | 5 | 5 | 5 | 5 | 0 | 0 | 0 | 0 |
| Example 21 | Compound of Preparation Example 21 | 50 | 5 | 5 | 5 | 5 | 5 | 5 | 5 | 5 | 0 | 0 | 0 | 0 |
| | | 25 | 5 | 5 | 5 | 5 | 5 | 5 | 5 | 5 | 0 | 0 | 0 | 0 |
| Example 22 | Compound of Preparation Example 22 | 100 | 5 | 5 | 5 | 5 | 5 | 5 | 5 | 5 | 0 | 0 | 0 | 0 |
| | | 50 | 5 | 5 | 5 | 5 | 5 | 5 | 5 | 5 | 0 | 0 | 0 | 0 |
| Example 23 | Compound of Preparation Example 23 | 25 | 5 | 5 | 5 | 5 | 5 | 5 | 5 | 5 | 0 | 0 | 0 | 0 |
| | | 100 | 5 | 5 | 5 | 5 | 5 | 5 | 5 | 5 | 0 | 0 | 0 | 0 |
| Example 24 | Compound of Preparation Example 24 | 50 | 5 | 5 | 5 | 5 | 5 | 5 | 5 | 5 | 0 | 0 | 0 | 0 |
| | | 25 | 5 | 5 | 5 | 5 | 5 | 5 | 5 | 5 | 0 | 0 | 0 | 0 |
| Example 25 | Compound of Preparation Example 25 | 100 | 5 | 5 | 5 | 5 | 5 | 5 | 5 | 5 | 0 | 0 | 0 | 0 |
| | | 50 | 5 | 5 | 5 | 5 | 5 | 5 | 5 | 5 | 0 | 0 | 0 | 0 |
| Example 26 | Compound of Preparation Example 26 | 25 | 5 | 5 | 5 | 5 | 5 | 5 | 5 | 5 | 0 | 0 | 0 | 0 |
| | | 100 | 5 | 5 | 5 | 5 | 5 | 5 | 5 | 5 | 0 | 0 | 0 | 0 |
| Example 27 | Compound of Preparation Example 27 | 50 | 5 | 5 | 5 | 5 | 5 | 5 | 5 | 5 | 0 | 0 | 0 | 0 |
| | | 25 | 5 | 5 | 5 | 5 | 5 | 5 | 5 | 5 | 0 | 0 | 0 | 0 |
| Example 28 | Compound of Preparation Example 28 | 100 | 5 | 5 | 5 | 5 | 5 | 5 | 5 | 5 | 0 | 0 | 0 | 0 |
| | | 50 | 5 | 5 | 5 | 5 | 5 | 5 | 5 | 5 | 0 | 0 | 0 | 0 |
| Example 29 | Compound of Preparation Example 29 | 25 | 5 | 5 | 5 | 5 | 5 | 5 | 5 | 5 | 0 | 0 | 0 | 0 |
| | | 100 | 5 | 5 | 5 | 5 | 5 | 5 | 5 | 5 | 0 | 0 | 0 | 0 |
| Example 30 | Compound of Preparation Example 30 | 50 | 5 | 5 | 5 | 5 | 5 | 5 | 5 | 5 | 0 | 0 | 0 | 0 |
| | | 25 | 5 | 5 | 5 | 5 | 5 | 5 | 5 | 5 | 0 | 0 | 0 | 0 |
| Example 31 | Compound of Preparation Example 31 | 100 | 5 | 5 | 5 | 5 | 5 | 5 | 5 | 5 | 0 | 0 | 0 | 0 |
| Example | Compound of | 100 | 5 | 5 | 5 | 5 | 5 | 5 | 5 | 5 | 0 | 0 | 0 | 0 |

TABLE 4-continued

| No. | Compound used | Amount of herbicide (g/10a) | Herbicidal effect ||||||||| Phytotoxicity ||||
|---|---|---|---|---|---|---|---|---|---|---|---|---|---|---|
| | | | Alopecurus myosuroides | Digitaria sanguinalis | Abutilon theophrasti | Veronica persica | Polygonum persicaria | Viola arvensis | Amaranthus patulus | Galium sparium var. echinospermon | Wheat | Barley | Corn | Grain sorghum |
| Example 32 | Preparation Example 32 | 50 | 5 | 5 | 5 | 5 | 5 | 5 | 5 | 5 | 0 | 0 | 0 | 0 |
| | Compound of | 25 | 5 | 5 | 5 | 5 | 5 | 5 | 5 | 5 | 0 | 0 | 0 | 0 |
| Example 33 | Preparation Example 33 | 100 | 5 | 5 | 5 | 5 | 5 | 5 | 5 | 5 | 0 | 0 | 0 | 0 |
| | Compound of | 50 | 5 | 5 | 5 | 5 | 5 | 5 | 5 | 5 | 0 | 0 | 0 | 0 |
| Example 34 | Preparation Example 34 | 100 | 5 | 5 | 5 | 5 | 5 | 5 | 5 | 5 | 0 | 0 | 0 | 0 |
| | Compound of | 50 | 5 | 5 | 5 | 5 | 5 | 5 | 5 | 5 | 0 | 0 | 0 | 0 |
| Example 35 | Preparation Example 35 | 25 | 5 | 5 | 5 | 5 | 5 | 5 | 5 | 5 | 0 | 0 | 0 | 0 |
| | Compound of | 100 | 5 | 5 | 5 | 5 | 5 | 5 | 5 | 5 | 0 | 0 | 0 | 0 |
| Example 36 | Preparation Example 36 | 50 | 5 | 5 | 5 | 5 | 5 | 5 | 5 | 5 | 0 | 0 | 0 | 0 |
| | Compound of | 25 | 5 | 5 | 5 | 5 | 5 | 5 | 5 | 5 | 0 | 0 | 0 | 0 |
| Example 37 | Preparation Example 37 | 100 | 5 | 5 | 5 | 5 | 5 | 5 | 5 | 5 | 0 | 0 | 0 | 0 |
| | Compound of | 50 | 5 | 5 | 5 | 5 | 5 | 5 | 5 | 5 | 0 | 0 | 0 | 0 |
| Example 38 | Preparation Example 38 | 25 | 5 | 5 | 5 | 5 | 5 | 5 | 5 | 5 | 0 | 0 | 0 | 0 |
| | Compound of | 100 | 5 | 5 | 5 | 5 | 5 | 5 | 5 | 5 | 0 | 0 | 0 | 0 |
| Example 39 | Preparation Example 39 | 50 | 5 | 5 | 5 | 5 | 5 | 5 | 5 | 5 | 0 | 0 | 0 | 0 |
| | Compound of | 25 | 5 | 5 | 5 | 5 | 5 | 5 | 5 | 5 | 0 | 0 | 0 | 0 |
| Example 40 | Preparation Example 40 | 100 | 5 | 5 | 5 | 5 | 5 | 5 | 5 | 5 | 0 | 0 | 0 | 0 |
| | Compound of | 50 | 5 | 5 | 5 | 5 | 5 | 5 | 5 | 5 | 0 | 0 | 0 | 0 |
| Example 41 | Preparation Example 41 | 25 | 5 | 5 | 5 | 5 | 5 | 5 | 5 | 5 | 0 | 0 | 0 | 0 |
| | Compound of | 100 | 4 | 3 | 4 | 4 | 4 | 4 | 4 | 4 | 0 | 0 | 0 | 0 |
| Comparative Example 1 | Triazine derivative A | 50 | 3 | 3 | 2 | 3 | 3 | 3 | 3 | 2 | 0 | 0 | 0 | 0 |
| | | 25 | 1 | 1 | 2 | 4 | 2 | 2 | 3 | 1 | 0 | 0 | 0 | 0 |
| Comparative Example 2 | Triazine derivative B | 100 | 3 | 3 | 4 | 4 | 3 | 3 | 4 | 2 | 0 | 0 | 0 | 0 |
| | | 50 | 1 | 1 | 3 | 3 | 2 | 3 | 3 | 0 | 0 | 0 | 0 | 0 |
| Comparative Example 3 | Triazine derivative C | 100 | 5 | 5 | 4 | 5 | 5 | 5 | 5 | 5 | 0 | 0 | 0 | 0 |
| | | 50 | 3 | 3 | 4 | 4 | 4 | 4 | 5 | 3 | 0 | 0 | 0 | 0 |
| Comparative Example 4 | Triazine derivative D | 100 | 2 | 2 | 4 | 3 | 2 | 2 | 4 | 1 | 0 | 0 | 0 | 0 |
| | | 50 | 3 | 5 | 3 | 5 | 5 | 4 | 4 | 3 | 0 | 0 | 0 | 0 |
| Comparative Example 5 | Triazine derivative E | 100 | 1 | 2 | 3 | 3 | 3 | 2 | 2 | 1 | 0 | 0 | 0 | 0 |
| | | 50 | 0 | 0 | 1 | 0 | 0 | 0 | 0 | 2 | 0 | 0 | 0 | 0 |
| | | 25 | 3 | 5 | 4 | 5 | 4 | 4 | 5 | 0 | 0 | 0 | 0 | 0 |
| Comparative Example 6 | Triazine derivative F | 100 | 2 | 3 | 3 | 4 | 3 | 4 | 3 | 4 | 0 | 0 | 0 | 0 |
| | | 50 | 0 | 1 | 2 | 2 | 1 | 2 | 0 | 3 | 0 | 0 | 0 | 0 |
| | | 25 | | | | | | | | 1 | 0 | 0 | 0 | 0 |

EXAMPLES 42 TO 82

Foilage Treatment Test

Seeds of weeds including *Abutilon theophrasti*, Common blackjack, *Amaranthus patulus*, *Cassia obtusifolia*, *Ipomoea purpurea*, *Galium sparium var. echinospermon*, *Veronica persica* and seeds of crops including corn, grain sorghum, wheat, barley and oat were sowed on to the Wagner pots of 1/2000 filled with soil of upland field and, after covering up with soil, were grown in a greenhouse and, when the weeds were in their mono- to bi-foliate period and the crops were in their tri-foliate period, an aqueous suspension of a specified amount of the herbicide prepared in the above described Formulation Example 6 was uniformly sprinkled by spraying to the parts of stems and leaves in a liquid volume corresponding to 100 liters/10 ares. Thereafter, they were grown in a greenhouse and the phytotoxicity on the crops and the herbicidal effects were estimated according to the following criteria on the 20th day of the treatment. The results are shown in Table 5.

[Criteria of estimation]

| Degree of herbicidal effects | Herbicidal effects (% killed weeds) |
|---|---|
| 0 | less than 5% (almost no effects) |
| 1 | 5 to 20% |
| 2 | 20 to 40% |
| 3 | 40 to 70% |
| 4 | 70 to 80% |
| 5 | 90% or more (almost complete withering) |

The % killed weeds given above was obtained from the following equation by determining the over,round raw grass weight in the phytotoxicity treated zone and the overground raw grass weight in the untreated zone.

killed weeds, % =

$$\left( 1 - \frac{\text{overground raw grass weight in treated zone}}{\text{overground raw grass weight in untreated zone}} \right) \times 100$$

Degree of phytotoxicity
0 ... no phytotoxicity to crops
1 ... almost no phytotoxicity to crops
2 ... little but noticeable phytotoxicity to crops
3 ... noticeable phytotoxicity to crops
4 ... remarkably strong phytotoxicity to crops
5 ... almost complete withering of crops

COMPARATIVE EXAMPLES 7 TO 12

The same procedure as in Example g was undertaken excepting the use of the triazine derivative A, B, C, D, E or F shown in Comparative Examples 1 to 6 in place of the triazine derivative prepared in Preparation Example 1, in Example 42. The results are shown in Table 5.

TABLE 5

| No. | Compound used | Amount of herbicide (g/10a) | Phytotoxicity | | | | | Herbicidal effect | | | | | | |
|---|---|---|---|---|---|---|---|---|---|---|---|---|---|---|
| | | | Corn | Grain sorghum | Wheat | Barley | Oats | Abutilon theophrasti | Common blackjack | Amaranthus patulus | Cassia obtusifolia L. | Ipomoea purpurea | Galium sparium var. echinospermon | Veronica persica |
| Example 42 | Compound of Preparation Example 1 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 43 | Compound of Preparation Example 2 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 44 | Compound of Preparation Example 3 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 45 | Compound of Preparation Example 4 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 46 | Compound of Preparation Example 5 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 47 | Compound of Preparation Example 6 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 48 | Compound of Preparation Example 7 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 49 | Compound of Preparation Example 8 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |

TABLE 5-continued

| No. | Compound used | Amount of herbicide (g/10a) | Phytotoxicity | | | | | Herbicidal effect | | | | | | |
|---|---|---|---|---|---|---|---|---|---|---|---|---|---|---|
| | | | Corn | Grain sorghum | Wheat | Barley | Oats | Abutilon theophrasti | Common blackjack | Amaranthus patulus | Cassia obtusifolia L. | Ipomoea purpurea | Galium sparium var. echinospermon | Veronica persica |
| Example 50 | Compound of Preparation Example 9 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 51 | Compound of Preparation Example 10 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 52 | Compound of Preparation Example 11 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 53 | Compound of Preparation Example 12 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 54 | Compound of Preparation Example 13 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 55 | Compound of Preparation Example 14 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 56 | Compound of Preparation Example 15 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 57 | Compound of Preparation Example 16 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |

TABLE 5-continued

| No. | Compound used | Amount of herbicide (g/10a) | Phytotoxicity | | | | | Herbicidal effect | | | | | | |
|---|---|---|---|---|---|---|---|---|---|---|---|---|---|---|
| | | | Corn | Grain sorghum | Wheat | Barley | Oats | Abutilon theophrasti | Common blackjack | Amaranthus patulus | Cassia obtusifolia L. | Ipomoea purpurea | Galium sparium var. echinospermon | Veronica persica |
| Example 58 | Compound of Preparation Example 17 | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 59 | Compound of Preparation Example 18 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 60 | Compound of Preparation Example 19 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 61 | Compound of Preparation Example 20 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 62 | Compound of Preparation Example 21 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 63 | Compound of Preparation Example 22 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 64 | Compound of Preparation Example 23 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 65 | Compound of Preparation Example 24 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |

TABLE 5-continued

|  |  | Amount of herbicide (g/10a) | Phytotoxicity | | | | | Herbicidal effect | | | | | | |
|---|---|---|---|---|---|---|---|---|---|---|---|---|---|---|
| No. | Compound used | | Corn | Grain sorghum | Wheat | Barley | Oats | Abutilon theophrasti | Common blackjack | Amaranthus patulus | Cassia obtusifolia L. | Ipomoea purpurea | Galium spurium var. echinospermon | Veronica persica |
| Example 66 | Compound of Preparation Example 25 | 50 | 0 | 0 | 0 | 0 | 0 | 5 | 5 | 5 | 5 | 5 | 5 | 5 |
|  |  | 25 | 0 | 0 | 0 | 0 | 0 | 5 | 5 | 5 | 5 | 5 | 5 | 5 |
|  |  | 12.5 | 0 | 0 | 0 | 0 | 0 | 5 | 5 | 5 | 5 | 5 | 5 | 5 |
| Example 67 | Compound of Preparation Example 26 | 400 | 0 | 0 | 0 | 0 | 0 | 5 | 5 | 5 | 5 | 5 | 5 | 5 |
|  |  | 200 | 0 | 0 | 0 | 0 | 0 | 5 | 5 | 5 | 5 | 5 | 5 | 5 |
|  |  | 100 | 0 | 0 | 0 | 0 | 0 | 5 | 5 | 5 | 5 | 5 | 5 | 5 |
|  |  | 50 | 0 | 0 | 0 | 0 | 0 | 5 | 5 | 5 | 5 | 5 | 5 | 5 |
|  |  | 25 | 0 | 0 | 0 | 0 | 0 | 5 | 5 | 5 | 5 | 5 | 5 | 5 |
|  |  | 12.5 | 0 | 0 | 0 | 0 | 0 | 5 | 5 | 5 | 5 | 5 | 5 | 5 |
| Example 68 | Compound of Preparation Example 27 | 400 | 0 | 0 | 0 | 0 | 0 | 5 | 5 | 5 | 5 | 5 | 5 | 5 |
|  |  | 200 | 0 | 0 | 0 | 0 | 0 | 5 | 5 | 5 | 5 | 5 | 5 | 5 |
|  |  | 100 | 0 | 0 | 0 | 0 | 0 | 5 | 5 | 5 | 5 | 5 | 5 | 5 |
|  |  | 50 | 0 | 0 | 0 | 0 | 0 | 5 | 5 | 5 | 5 | 5 | 5 | 5 |
|  |  | 25 | 0 | 0 | 0 | 0 | 0 | 5 | 5 | 5 | 5 | 5 | 5 | 5 |
|  |  | 12.5 | 0 | 0 | 0 | 0 | 0 | 5 | 5 | 5 | 5 | 5 | 5 | 5 |
| Example 69 | Compound of Preparation Example 28 | 400 | 0 | 0 | 0 | 0 | 0 | 5 | 5 | 5 | 5 | 5 | 5 | 5 |
|  |  | 200 | 0 | 0 | 0 | 0 | 0 | 5 | 5 | 5 | 5 | 5 | 5 | 5 |
|  |  | 100 | 0 | 0 | 0 | 0 | 0 | 5 | 5 | 5 | 5 | 5 | 5 | 5 |
|  |  | 50 | 0 | 0 | 0 | 0 | 0 | 5 | 5 | 5 | 5 | 5 | 5 | 5 |
|  |  | 25 | 0 | 0 | 0 | 0 | 0 | 5 | 5 | 5 | 5 | 5 | 5 | 5 |
|  |  | 12.5 | 0 | 0 | 0 | 0 | 0 | 5 | 5 | 5 | 5 | 5 | 5 | 5 |
| Example 70 | Compound of Preparation Example 29 | 400 | 0 | 0 | 0 | 0 | 0 | 5 | 5 | 5 | 5 | 5 | 5 | 5 |
|  |  | 200 | 0 | 0 | 0 | 0 | 0 | 5 | 5 | 5 | 5 | 5 | 5 | 5 |
|  |  | 100 | 0 | 0 | 0 | 0 | 0 | 5 | 5 | 5 | 5 | 5 | 5 | 5 |
|  |  | 50 | 0 | 0 | 0 | 0 | 0 | 5 | 5 | 5 | 5 | 5 | 5 | 5 |
|  |  | 25 | 0 | 0 | 0 | 0 | 0 | 5 | 5 | 5 | 5 | 5 | 5 | 5 |
|  |  | 12.5 | 0 | 0 | 0 | 0 | 0 | 5 | 5 | 5 | 5 | 5 | 5 | 5 |
| Example 71 | Compound of Preparation Example 30 | 400 | 0 | 0 | 0 | 0 | 0 | 5 | 5 | 5 | 5 | 5 | 5 | 5 |
|  |  | 200 | 0 | 0 | 0 | 0 | 0 | 5 | 5 | 5 | 5 | 5 | 5 | 5 |
|  |  | 100 | 0 | 0 | 0 | 0 | 0 | 5 | 5 | 5 | 5 | 5 | 5 | 5 |
|  |  | 50 | 0 | 0 | 0 | 0 | 0 | 5 | 5 | 5 | 5 | 5 | 5 | 5 |
|  |  | 25 | 0 | 0 | 0 | 0 | 0 | 5 | 5 | 5 | 5 | 5 | 5 | 5 |
|  |  | 12.5 | 0 | 0 | 0 | 0 | 0 | 5 | 5 | 5 | 5 | 5 | 5 | 5 |
| Example 72 | Compound of Preparation Example 31 | 400 | 0 | 0 | 0 | 0 | 0 | 5 | 5 | 5 | 5 | 5 | 5 | 5 |
|  |  | 200 | 0 | 0 | 0 | 0 | 0 | 5 | 5 | 5 | 5 | 5 | 5 | 5 |
|  |  | 100 | 0 | 0 | 0 | 0 | 0 | 5 | 5 | 5 | 5 | 5 | 5 | 5 |
|  |  | 50 | 0 | 0 | 0 | 0 | 0 | 5 | 5 | 5 | 5 | 5 | 5 | 5 |
|  |  | 25 | 0 | 0 | 0 | 0 | 0 | 5 | 5 | 5 | 5 | 5 | 5 | 5 |
|  |  | 12.5 | 0 | 0 | 0 | 0 | 0 | 5 | 5 | 5 | 5 | 5 | 5 | 5 |
| Example 73 | Compound of Preparation | 400 | 0 | 0 | 0 | 0 | 0 | 5 | 5 | 5 | 5 | 5 | 5 | 5 |
|  |  | 200 | 0 | 0 | 0 | 0 | 0 | 5 | 5 | 5 | 5 | 5 | 5 | 5 |

TABLE 5-continued

|  |  | Amount of | Phytotoxicity | | | | | Herbicidal effect | | | | | | |
|---|---|---|---|---|---|---|---|---|---|---|---|---|---|---|
| No. | Compound used | herbicide (g/10a) | Corn | Grain sorghum | Wheat | Barley | Oats | Abutilon theophrasti | Common blackjack | Amaranthus patulus | Cassia obtusifolia L. | Ipomoea purpurea | Galium sparium var. echinospermon | Veronica persica |
| Example 74 | Compound of Example 32 | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 75 | Compound of Preparation Example 33 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 76 | Compound of Preparation Example 34 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 77 | Compound of Preparation Example 35 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 78 | Compound of Preparation Example 36 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 79 | Compound of Preparation Example 37 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 80 | Compound of Preparation Example 38 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example | Compound of Preparation Example 39 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example | Compound of | 400 | 0 | 0 | 0 | 0 | 0 | 5 | 5 | 5 | 5 | 5 | 5 | 5 |

TABLE 5-continued

| | | | Phytotoxicity | | | | | Herbicidal effect | | | | | | |
|---|---|---|---|---|---|---|---|---|---|---|---|---|---|---|
| No. | Compound used | Amount of herbicide (g/10a) | Corn | Grain sorghum | Wheat | Barley | Oats | Abutilon theophrasti | Common blackjack | Amaranthus patulus | Cassia obtusifolia L. | Ipomoea purpurea | Galium sparium var. echinospermon | Veronica persica |
| 81 | Preparation Example 40 | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Example 82 | Compound of Preparation Example 41 | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 4 | 3 | 3 | 2 | 4 |
| | | 12.5 | 0 | 0 | 0 | 0 | 0 | 3 | 3 | 2 | 2 | 2 | 1 | 3 |
| Comparative Example 7 | Triazine derivative B | 400 | 0 | 0 | 0 | 0 | 0 | 1 | 2 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 5 | 5 | 5 | 5 | 5 | 5 | 5 |
| | | 50 | 0 | 0 | 0 | 0 | 0 | 3 | 3 | 4 | 4 | 3 | 3 | 4 |
| | | 25 | 0 | 0 | 0 | 0 | 0 | 2 | 2 | 4 | 2 | 2 | 2 | 2 |
| | | 12.5 | 0 | 0 | 0 | 0 | 0 | 2 | 2 | 2 | 1 | 2 | 1 | 2 |
| Comparative Example 8 | Triazine derivative C | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 3 | 3 | 4 | 4 | 3 | 3 | 4 |
| | | 50 | 0 | 0 | 0 | 0 | 0 | 3 | 3 | 4 | 2 | 3 | 2 | 3 |
| | | 25 | 0 | 0 | 0 | 0 | 0 | 2 | 2 | 2 | 1 | 2 | 1 | 2 |
| | | 12.5 | 0 | 0 | 0 | 0 | 0 | 2 | 2 | 2 | 1 | 2 | 1 | 2 |
| Comparative Example 9 | Triazine derivative D | 400 | 0 | 0 | 0 | 0 | 0 | 5 | 5 | 5 | 5 | 5 | 5 | 5 |
| | | 200 | 0 | 0 | 0 | 0 | 0 | 5 | 5 | 5 | 5 | 5 | 5 | 5 |
| | | 100 | 0 | 0 | 0 | 0 | 0 | 4 | 4 | 4 | 4 | 4 | 4 | 4 |
| | | 50 | 0 | 0 | 0 | 0 | 0 | 2 | 2 | 4 | 2 | 3 | 3 | 3 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Comparative Example 10 | Triazine derivative E | 400 | 0 | 0 | 0 | 0 | 0 | 5 | 4 | 4 | 4 | 4 | 4 | 4 |
| | | 200 | 0 | 0 | 0 | 0 | 0 | 4 | 4 | 4 | 3 | 3 | 3 | 3 |
| | | 100 | 0 | 0 | 0 | 0 | 0 | 3 | 3 | 4 | 2 | 2 | 2 | 2 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 4 | 4 | 3 | 4 |
| Comparative Example 11 | Triazine derivative F | 400 | 0 | 0 | 0 | 0 | 0 | 3 | 3 | 4 | 3 | 3 | 3 | 3 |
| | | 200 | 0 | 0 | 0 | 0 | 0 | 3 | 3 | 5 | 3 | 3 | 2 | 2 |
| | | 100 | 0 | 0 | 0 | 0 | 0 | 3 | 3 | 5 | 2 | 2 | 2 | 1 |
| | | 50 | 0 | 0 | 0 | 0 | 0 | 5 | 5 | 5 | 5 | 5 | 5 | 5 |
| | | 25 | 0 | 0 | 0 | 0 | 0 | 5 | 5 | 5 | 5 | 5 | 5 | 5 |
| | | 12.5 | 0 | 0 | 0 | 0 | 0 | 5 | 5 | 5 | 5 | 5 | 5 | 5 |
| Comparative Example 12 | Triazine derivative G | 400 | 0 | 0 | 0 | 0 | 0 | 5 | 4 | 5 | 4 | 4 | 3 | 4 |
| | | 200 | 0 | 0 | 0 | 0 | 0 | 4 | 5 | 5 | 3 | 3 | 3 | 3 |
| | | 100 | 0 | 0 | 0 | 0 | 0 | 3 | 4 | 5 | 2 | 3 | 2 | 2 |
| | | 50 | 0 | 0 | 0 | 0 | 0 | 5 | 5 | 5 | 5 | 5 | 5 | 5 |
| | | 25 | 0 | 0 | 0 | 0 | 0 | 4 | 5 | 5 | 4 | 4 | 4 | 4 |
| | | 12.5 | 0 | 0 | 0 | 0 | 0 | 1 | 4 | 5 | 2 | 3 | 3 | 3 |

EXAMPLES 83 TO 123

Paddy Soil Treatment Test

Porcelain pots of 1/15500 are were filled with a paddy field soil and seeds of *Echinochola crus-galli P. Beauv. var formosensis Ohwi*, *Cyperus difformis L.*, broad-leaved weeds (*Rotala indica* (Willd) *Koehne var. uligirosa* (Miq.) *Koehne* and *Monochoria vaginalis Presl var. plantaginea*) and *Scirpus juncoides Roxb. ssp. Hotarui Ohwi T. Koyama* were uniformly sowed to the surface layer and further tubers of *Cyperus serotinus* Rottb. and *Sagittaria pygrmaea* Miq. were transplanted followed by transplantation of paddy rice in the bifoliate period.

Before germination of the weeds, thereafter, a specified volume of a diluted solution of the herbicide obtained in the above described Formulation Example 6 was uniformly dropped to the water surface to effect treatment followed by standing of the pcts in a greenhouse with periodical sprinkling of water.

Table 6 shows the results in the investigations of the herbicidal effects and phytotoxicity to the rice crop after 20 days from the treatment with the herbicide solution, Incidentally, the dose is given by the amount of the effective ingredient per 10 ares. And, the phytotoxicity to paddy rice and the herbicidal effects are expressed as shown below by determining the respective air-dried weights.

| Extent of phytotoxicity | Phytotoxicity to paddy rice (relative to untreated zone) |
|---|---|
| 0 | 100% |
| 1 | 95 to 99% |
| 2 | 90 to 94% |
| 3 | 80 to 89% |
| 4 | 60 to 79% |
| 5 | 50 to 59% |

| Degree of herbicidal effects | Herbicidal effects (relative to untreated zone) |
|---|---|
| 0 | 100% |
| 1 | 61 to 99% |
| 2 | 21 to 60% |
| 3 | 11 to 20% |
| 4 | 1 to 10% |
| 5 | 0% |

COMPARATIVE EXAMPLES 13 TO 18

The same procedure as in Example 11 was undertaken excepting the use of the triazine derivative A, B, C, D, E or F shown in Comparative Examples 1 to 6 in place of the triazine derivative prepared in Preparation Example 1, in Example 83. The results are shown in Table 6.

TABLE 6

| No. | Compound used | Amount of herbicide (g/10a) | Echinochoia crus-galli P. Beauv. var. formosensis Ohwi | Cyperus serotinus Rottb. | Scirpus juncoides Roxb. ssp. Hotarui Ohwi T. Koyama | Cyperus difformis L. | Broadleaf weeds | Sagittaria pygmaea Miq. | Paddy rice plants |
|---|---|---|---|---|---|---|---|---|---|
| Example 83 | Compound of Preparation Example 1 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | — | 5 | 5 | 0 |
|  |  | 12.5 | 5 | 5 | 5 | 5 | 5 | 5 | 0 |
| Example 84 | Compound of Preparation Example 2 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |
|  |  | 12.5 | 5 | 5 | 5 | 5 | 5 | 5 | 0 |
| Example 85 | Compound of Preparation Example 3 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |
|  |  | 12.5 | 5 | 5 | 5 | 5 | 5 | 5 | 0 |
| Example 86 | Compound of Preparation Example 4 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |
|  |  | 12.5 | 5 | 5 | 5 | 5 | 5 | 5 | 0 |
| Example 87 | Compound of Preparation Example 5 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |
|  |  | 12.5 | 5 | 5 | 5 | 5 | 5 | 5 | 0 |
| Example 88 | Compound of Preparation Example 6 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |
|  |  | 12.5 | 5 | 5 | 5 | 5 | 5 | 5 | 0 |
| Example 89 | Compound of Preparation Example 7 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |
|  |  | 12.5 | 5 | 5 | 5 | 5 | 5 | 5 | 0 |
| Example 90 | Compound of Preparation Example 8 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |
|  |  | 12.5 | 5 | 5 | 5 | 5 | 5 | 5 | 0 |
| Example 91 | Compound of Preparation Example 9 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |
|  |  | 12.5 | 5 | 5 | 5 | 5 | 5 | 5 | 0 |
| Example 92 | Compound of Preparation Example 10 | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |
|  |  | 12.5 | 5 | 5 | 5 | 5 | 5 | 5 | 0 |
| Example 93 | Compound of Preparation | 100 | 5 | 5 | 5 | 5 | 5 | 5 | 0 |
|  |  | 50 | 5 | 5 | 5 | 5 | 5 | 5 | 0 |
|  |  | 25 | 5 | 5 | 5 | 5 | 5 | 5 | 0 |

TABLE 6-continued

| No. | Compound used | Amount of herbicide (g/10a) | Echinochoia crus-galli P. Beauv. var. formosensis Ohwi | Cyperus serotinus Rottb. | Scirpus juncoides Roxb. ssp. Hotarui Ohwi T. Koyama | Cyperus difformis L. | Broadleaf weeds | Sagittaria pygmaea Miq. | Paddy rice plants |
|---|---|---|---|---|---|---|---|---|---|
| | Example 11 | 12.5 | 5 | 5 | 5 | 5 | 5 | 5 | 0 |
| Example 94 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 12 | 12.5 | 5 | 5 | 5 | 5 | 5 | 5 | 0 |
| Example 95 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 13 | 12.5 | 5 | 5 | 5 | 5 | 5 | 5 | 0 |
| Example 96 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 14 | 12.5 | 5 | 5 | 5 | 5 | 5 | 5 | 0 |
| Example 97 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 15 | 12.5 | 5 | 5 | 5 | 5 | 5 | 5 | 0 |
| Example 98 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 16 | 12.5 | 5 | 5 | 5 | 5 | 5 | 5 | 0 |
| Example 99 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 17 | 12.5 | 5 | 5 | 5 | 5 | 5 | 5 | 0 |
| Example 100 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 18 | 12.5 | 5 | 5 | 5 | 5 | 5 | 5 | 0 |
| Example 101 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 19 | 12.5 | 5 | 5 | 5 | 5 | 5 | 5 | 0 |
| Example 102 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 20 | 12.5 | 5 | 5 | 5 | 5 | 5 | 5 | 0 |
| Example 103 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 21 | 12.5 | 5 | 5 | 5 | 5 | 5 | 5 | 0 |
| Example 104 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 22 | 12.5 | 5 | 5 | 5 | 5 | 5 | 5 | 0 |
| Example 105 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 23 | 12.5 | 5 | 5 | 5 | 5 | 5 | 5 | 0 |
| Example 106 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 24 | 12.5 | 5 | 5 | 5 | 5 | 5 | 5 | 0 |
| Example 107 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 25 | 12.5 | 5 | 5 | 5 | 5 | 5 | 5 | 0 |
| Example 108 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 26 | 12.5 | 5 | 5 | 5 | 5 | 5 | 5 | 0 |
| Example 109 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 27 | 12.5 | 5 | 5 | 5 | 5 | 5 | 5 | 0 |
| Example 110 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 28 | 12.5 | 5 | 5 | 5 | 5 | 5 | 5 | 0 |
| Example 111 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 29 | 12.5 | 5 | 5 | 5 | 5 | 5 | 5 | 0 |
| Example 112 | Compound of | 100 | 5 | 5 | 5 | 5 | 5 | 5 | 0 |
| | | 50 | 5 | 5 | 5 | 5 | 5 | 5 | 0 |
| | Preparation | 25 | 5 | 5 | 5 | 5 | 5 | 5 | 0 |
| | Example 30 | 12.5 | 5 | 5 | 5 | 5 | 5 | 5 | 0 |
| Example | Compound | 100 | 5 | 5 | 5 | 5 | 5 | 5 | 0 |

TABLE 6-continued

| No. | Compound used | Amount of herbicide (g/10a) | Herbicidal effect | | | | | | Paddy rice plants |
|---|---|---|---|---|---|---|---|---|---|
| | | | Echinochoia crus-galli P. Beauv. var. formosensis Ohwi | Cyperus serotinus Rottb. | Scirpus juncoides Roxb. ssp. Hotarui Ohwi T. Koyama | Cyperus difformis L. | Broadleaf weeds | Sagittaria pygmaea Miq. | |
| 113 | of Preparation Example 31 | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 114 | Compound of Preparation Example 32 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 115 | Compound of Preparation Example 33 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 116 | Compound of Preparation Example 34 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 117 | Compound of Preparation Example 35 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 118 | Compound of Preparation Example 36 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 119 | Compound of Preparation Example 37 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 120 | Compound of Preparation Example 38 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 121 | Compound of Preparation Example 39 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 122 | Compound of Preparation Example 40 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Example 123 | Compound of Preparation Example 41 | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 5 | 5 | 5 | 5 | 0 |
| Comparative Example 13 | Triazine derivative A | 100 | 5 | 5 | 5 | 5 | 5 | 5 | 0 |
| | | 50 | 5 | 5 | 4 | 5 | 4 | 5 | 0 |
| | | 25 | 5 | 4 | 3 | 5 | 4 | 3 | 0 |
| | | 12.5 | 5 | 4 | 2 | 5 | 4 | 2 | 0 |
| Comparative Example 14 | Triazine derivative B | 100 | 5 | 4 | 5 | 5 | 5 | 5 | 0 |
| | | 50 | 5 | 4 | 5 | 5 | 4 | 5 | 0 |
| | | 25 | 5 | 3 | 4 | 5 | 4 | 3 | 0 |
| | | 12.5 | 5 | 3 | 2 | 5 | 4 | 2 | 0 |
| Comparative Example 15 | Triazine derivative C | 100 | 5 | 5 | 5 | 5 | 5 | 5 | 0 |
| | | 50 | 5 | 5 | 5 | 5 | 5 | 5 | 0 |
| | | 25 | 5 | 5 | 3 | 5 | 5 | 3 | 0 |
| | | 12.5 | 5 | 3 | 2 | 5 | 5 | 3 | 0 |
| Comparative Example 16 | Triazine derivative D | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 5 | 3 | 5 | 5 | 3 | 0 |
| Comparative Example 17 | Triazine derivative E | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 4 | 3 | 5 | 5 | 3 | 0 |
| Comparative Example 18 | Triazine derivative F | 100 | 5 | 5 | 5 | 5 | 5 | 5 | 0 |
| | | 50 | 5 | 5 | 5 | 5 | 5 | 5 | 0 |
| | | 25 | 5 | 5 | 5 | 5 | 5 | 5 | 0 |
| | | 12.5 | 5 | 3 | 4 | 5 | 5 | 3 | 0 |

UTILIZABILITY IN INDUSTRY

The triazine derivative of the present invention is a novel compound and can be efficiently utilized as a herbicide. The herbicide of the present invention with the said triazine derivative as the effective ingredient exhibits, as compared with conventional herbicides for upland field, excellent herbicidal effects against weeds including troublesome weeds without causing phytotoxicity to upland crops and, in particular, a remarkably high effect can be obtained by the treatment to the soil before preemergence or by the treatment to foliage in the fields of crops belonging to Gramineous crops. Further, the herbicides of the present invention exhibit higher effectiveness against troublesome weeds still with less phytotoxicity than hitherto known herbicides for paddy rice.

We claim:

1. A triazine compound of the formula

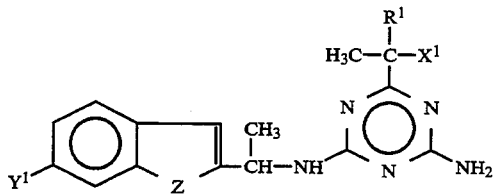

wherein $Y^1$ is a hydrogen atom or a methyl group and Z is an oxygen atom or a sulfur atom, $X^1$ is a halogen atom and $R^1$ is a hydrogen atom, a methyl group or an ethyl group, excluding the compound where $Y^1$ is hydrogen, $R^1$ is hydrogen and $X^1$ is chlorine.

2. The triazine compound of claim 1, wherein Z is a sulfur atom.

3. The triazine compound of claim 1, wherein Z is an oxygen atom.

4. The triazine compound of claim 1, wherein $X^1$ is a fluorine atom or a chlorine atom, $R^1$ is hydrogen or a methyl group.

5. The triazine compound of claim 1, wherein the compound is selected from the group consisting of
2-amino-4-[1-(benzofuran-2'-yl)ethylamino]-6-(α-fluoro, α-methyl ethyl)-s-triazine;
2-amino-4-[1-(benzofuran-2'-yl)ethylamino]-6-(α-chloro, α-methyl ethyl)-s-triazine;
2-amino-4-[1-(benzofuran-2'-yl)ethylamino]-6-(α-bromo, α-methyl ethyl)-s-triazine.
2-amino-4-[1-(benzofuran-2'-yl)ethylamino]-6-(α-fluoroethyl)-s-triazine;
2-amino-4-[1-(benzofuran-2'-yl)ethylamino]-6-(α-fluoro, α-methyl propyl)-s-triazine.
2-amino-4-[1-(benzothiophen-2'-yl)ethylamino]-6-(α-fluoro, α-methyl ethyl)-s-triazine.
2-amino-4-[1-(benzothiophen-2'-yl)ethylamino]-6-(α-chloro, α-methyl ethyl)-s-triazine;
2-amino-4-[1-(benzothiophen-2'-yl)ethylamino]-6-(α-fluoroethyl)-s-triazine;
2-amino-4-[1-(6'-methylbenzofuran-2'-yl)ethylamino]-6-(α-fluoro, α-methyl ethyl)-s-triazine;
2-amino-4-[1-(6'-methylbenzofuran-2'-yl)ethylamino]-6-(α- fluoroethyl)-s-triazine and
2-amino-4-[1-6'-methylbenzofuran-2'-yl)ethylamino]-6-(α-chloro, α-methyl ethyl)-s-triazine.

6. A herbicidal composition comprising an effective herbicidal amount of a triazine compound of claim 1 in admixture with a carrier.

7. The herbicidal composition according to claim 6, wherein the triazine compound is selected from the group consisting of
2-amino-4-[1-(benzofuran-2'-yl)ethylamino]-6-(α-fluoro, α-methyl ethyl)-s-triazine;
2-amino-4-[1-(benzofuran-2'-yl)ethylamino]-6-(α-chloro, α-methyl ethyl)-s-triazine;
2-amino-4-[1-(benzofuran-2'-yl)ethylamino]-6-(α-bromo, α-methyl ethyl)-s-triazine.
2-amino-4-[1-(benzofuran-2'-yl)ethylamino]-6-(α-fluoroethyl)-s-triazine;
2-amino-4-[1-(benzofuran-2'-yl)ethylamino]-6-(α-fluoro, α-methyl propyl)-s-triazine.
2-amino-4-[1-(benzothiophen-2'-yl)ethylamino]-6-(α-fluoro, α-methyl ethyl)-s-triazine.
2-amino-4-[1-(benzothiophen-2'-yl)ethylamino]-6-(α-chloro, α-methyl ethyl)-s-triazine;
2-amino-4-[1-(benzothiophen-2'-yl)ethylamino]-6-(α-fluoroethyl)-s-triazine;
2-amino-4-[1-(6'-methylbenzofuran-2'-yl)ethylamino]-6-(α-fluoro, α-methyl ethyl)-s-triazine;
2-amino-4-[1-(6'-methylbenzofuran-2'-yl)ethylamino]-6-(α- fluoroethyl)-s-triazine and
2-amino-4-[1-6'-methylbenzofuran-2'-yl)ethylamino]-6-(α-chloro, α-methyl ethyl)-s-triazine.

8. A method of combatting weeds comprising applying to weeds or to a locus thereof an effective herbicidal amount of a triazine compound of claim 1.

9. The method of combatting weeds according to claim 8, wherein the triazine compound is selected from the group consisting of
2-amino-4-[1-(benzofuran-2'-yl)ethylamino]-6-(α-fluoro, α-methyl ethyl)-s-triazine;
2-amino-4-[1-(benzofuran-2'-yl)ethylamino]-6-(α-chloro, α-methyl ethyl)-s-triazine;
2-amino-4-[1-(benzofuran-2'-yl)ethylamino]-6-(α-bromo, α-methyl ethyl)-s-triazine;
2-amino-4-[1-(benzofuran-2'-yl)ethylamino]-6-(α-fluoroethyl)-s-triazine;
2-amino-4-[1-(benzofuran-2'-yl)ethylamino]-6-(α-fluoro, α-methyl propyl)-s-triazine;
2-amino-4-[1-(benzothiophen-2'-yl)ethylamino]-6-(α-fluoro, α-methyl ethyl)-s-triazine.
2-amino-4-[1-(benzothiophen-2'-yl)ethylamino]-6-(α-chloro, α-methyl ethyl)-s-triazine;
2-amino-4-[1-(benzothiophen-2'-yl)ethylamino]-6-(α-fluoroethyl)-s-triazine;
2-amino-4-[1-(6'-methylbenzofuran-2'-yl)ethylamino]-6-(α-fluoro, α-methyl ethyl)-s-triazine;
2-amino-4-[1-(6'-methylbenzofuran-2'-yl)ethylamino]-6-(α-fluoroethyl)-s-triazine and
2-amino-4-[1-6'-methylbenzofuran-2'-yl)ethylamino]-6-(α-chloro, α-methyl ethyl)-s-triazine.

10. The method of combatting weeds according to claim 9, wherein said triazine compound is applied to a soil surface in an amount of 1 g/1 ares to 100 g/10 ares.

11. The method of combatting weeds according to claim 9, wherein the weeds are selected from the group consisting of *Alopecurus myosuroides, Digitaria sanguinalis, Abutilon theophrasti, Veronica persica, Polygonum persicaria, Viola arvensis, Amaranthus patulus* and *Galium sparium var. echinospermon.*

12. The method of combatting weeds according to claim 9, wherein said triazine compound is applied to a soil surface in an amount of 1 g/10 to 100 g/10 ares and the weeds are selected from the group consisting of *Alopecurus myosuroides, Digitaria Sanguinalis, Abutilon theophrasti, Veronica persica, Polygonum persicaria, Viola arvensis, Amaranthus patulus* and *Galium sparium var. echinospermon.*

13. The triazine compound of claim 1, wherein $R^1$ is a methyl group.

14. The triazine compound of claim 1, wherein $R^1$ is an ethyl group.

15. The triazine compound of claim 1, wherein $Y^1$ is a methyl group.

16. The triazine compound of claim 15, wherein Z is a sulfur atom.

17. 2-Amino-4-[-benzofuran-2'-yl)ethylamino]-6-(α-chloroethyl)-s-triazine.

18. A herbicidal composition comprising an effective herbicidal amount of 2-amino-4-[1-(benzofuran-2'-yl)ethylamino]-6-(α-chloroethyl)-s-triazine in admixture with a carrier.

19. A method of combatting weeds comprising applying to weeds or to a locus thereof an effective herbicidal amount of 2-amino-4-[1-(benzofuran-2'-yl)ethylamino]-6-(α-chloroethyl)-s-triazine.

20. The method of combatting weeds according to claim 19, wherein said triazine is applied to a soil surface in an amount of 1 g/1 ares to 100 g/10 ares.

21. The method of combatting weeds according to claim 19, wherein the weeds are selected from the group consisting of *Alopecurus myosuroides, Digitaria sanguinalis, Abutilon theophrasti, Veronica persica, Polygonum persicaria, Viola arvensis, Amaranthus patulus* and *Galium sparium var. echinospermon*.

22. The method of combatting weeds according to claim 19, wherein said triazine is applied to a soil surface in an amount of 1 g/10 to 100 g/10 ares and the weeds are selected from the group consisting of *Alopecurus myosuroides, Digitaria Sanguinalis, Abutilon theophrasti, Veronica persica, Polygonum persicaria, Viola arvensis, Amaranthus patulus* and *Galium sparium var. echinospermon*.

* * * * *

UNITED STATES PATENT AND TRADEMARK OFFICE
CERTIFICATE OF CORRECTION

PATENT NO. : 5,403,815
DATED : April 4, 1995
INVENTOR(S) : Nishii et al

It is certified that error appears in the above-indentified patent and that said Letters Patent is hereby corrected as shown below:

Title page, left column, on the line starting [62], after "Oct. 5, 1990" insert --which is a §371 of PCT/JP90/00194, filed, Feb. 19, 1990,--.

Title page, left column, bottom line, replace "Hirata et al" with --Nishii et al--.

Title page, right column, line 3, replace "63-14676" with --63-146876--.

Signed and Sealed this

Thirtieth Day of July, 1996

Attest:

BRUCE LEHMAN

*Attesting Officer*   *Commissioner of Patents and Trademarks*